(12) United States Patent
Miyamoto et al.

(10) Patent No.: US 7,794,470 B2
(45) Date of Patent: Sep. 14, 2010

(54) SURGICAL INSTRUMENT

(75) Inventors: Manabu Miyamoto, Hachioji (JP); Kazuo Banju, Hachioji (JP); Nobuaki Akui, Hino (JP); Shuhei Iizuka, Hamamatsu (JP)

(73) Assignee: Olympus Corporation, Tokyo (JP)

( * ) Notice: Subject to any disclaimer, the term of this patent is extended or adjusted under 35 U.S.C. 154(b) by 909 days.

(21) Appl. No.: 11/494,209

(22) Filed: Jul. 27, 2006

(65) Prior Publication Data
US 2006/0292917 A1 Dec. 28, 2006

Related U.S. Application Data

(63) Continuation of application No. PCT/JP2005/001097, filed on Jan. 27, 2005.

(30) Foreign Application Priority Data

Jan. 27, 2004 (JP) ............................. 2004-018925
Jan. 28, 2004 (JP) ............................. 2004-020481

(51) Int. Cl.
*A61B 17/04* (2006.01)

(52) U.S. Cl. ..................................... 606/144
(58) Field of Classification Search ................. 606/144, 606/139, 145, 148, 205, 207
See application file for complete search history.

(56) References Cited

U.S. PATENT DOCUMENTS

| 5,234,427 A | 8/1993 | Ohtomo et al. |
| 5,314,445 A * | 5/1994 | Heidmueller nee Degwitz et al. .......................... 606/208 |
| 5,951,575 A * | 9/1999 | Bolduc et al. ............... 606/144 |
| 5,976,121 A | 11/1999 | Matern et al. |
| 6,228,051 B1 | 5/2001 | Trumbull |
| 2002/0040217 A1 | 4/2002 | Jinno |
| 2002/0177857 A1 | 11/2002 | Otsuka et al. |
| 2003/0158576 A1 | 8/2003 | Nagase et al. |

FOREIGN PATENT DOCUMENTS

| EP | 0 423 757 A1 | 4/1991 |
| JP | 03-133443 | 6/1991 |
| JP | 08-164141 | 6/1996 |
| JP | 20022533554 | * 3/2001 |
| JP | 2003235857 | * 2/2002 |
| JP | 2002-102248 | 4/2002 |
| JP | 2002-345831 | 12/2002 |
| JP | 2003-2354857 | 8/2003 |
| WO | WO 96/07359 | 3/1996 |
| WO | WO 98/42260 | 10/1998 |

* cited by examiner

*Primary Examiner*—(Jackie) Tan-Uyen T Ho
*Assistant Examiner*—Christina Lauer
(74) *Attorney, Agent, or Firm*—Scully, Scott, Murphy & Presser, P.C.

(57) ABSTRACT

A surgical instrument comprises: a treatment unit provided at one end of the insertion unit, capable of turning about one axis, and comprising a clamping section capable of opening and closing action; an operation unit provided at the other end of the insertion unit; a turn force transmission mechanism and transmitting a turn force as a force to turn the treatment unit; an opening and closing force transmission mechanism and transmitting an opening and closing force as a force to open and close the clamping section; and a common operation mechanism, provided in the operation unit, which can generate the turn force transmitted by the turn force transmission mechanism and which can also generate the opening and closing force transmitted by the opening and closing transmission mechanism.

16 Claims, 30 Drawing Sheets

SURGICAL INSTRUMENT

CROSS REFERENCE TO RELATED APPLICATION

This application is a continuation application of PCT/JP2005/001097 filed on Jan. 27, 2005 and claims the benefit of Japanese Applications No. 2004-018925 filed in Japan on Jan. 27, 2004 and No. 2004-020481 filed in Japan on Jan. 28, 2004. The entire contents of these applications are incorporated herein by their reference.

BACKGROUND OF THE INVENTION

1. Field of the Invention

The present invention relates to a surgical instrument for holding a needle and suturing the tissues, for example, during the coronary artery bypass grafting of heart under the observation by an endoscope.

2. Description of the Related Art

The following procedure is known for conducting, for example, the coronary artery bypass grafting of heart under the observation by an endoscope. That is, a bypass procedure is known in which an endoscope, a surgical instrument as a needle-holder, and a forceps are inserted into a chest cavity via a trocar piercing a thoracic wall, part of the coronary artery is cut with the scissors-like forceps to provide an anastomotic opening, an internal thoracic artery is guided to the anastomotic opening with a grasping forceps, and the internal thoracic artery is connected by anastomosing to the anastomotic opening with the surgical instrument.

Furthermore, a surgical instrument having a structure comprising an insertion unit having a curved section at the distal end and also comprising jaws serving as a pair of treatment units at the distal end section of the insertion unit, those jaws being capable of opening and closing and turning about the axis of the insertion unit is known from U.S. Pat. No. 5,951,575 as a surgical instrument suitable for such a procedure, that is, as a needle-holder for holding a needle and anastomosing the tissue.

As described above, this surgical instrument has jaws serving as a treatment unit that can be opened, closed, and turned in the distal end section of the insertion unit. However, the turn of the jaws is carried out by turning a dial for turn operation that is provided in an operation unit, whereas the operation of opening and closing the jaws is carried out by operating an opening and closing lever that is provided in the operation unit.

SUMMARY OF THE INVENTION

The object of the present invention is to provide a surgical instrument of which the operation is facilitated.

The surgical instrument in accordance with a first aspect of the present invention comprises: an insertion unit; a treatment unit provided at one end of the insertion unit, capable of turning about one axis, and comprising a clamping section capable of opening and closing action; an operation unit provided at the other end of the insertion unit; a turn force transmission mechanism, provided between the operation unit and the treatment unit along the insertion unit, and transmitting a turn force as a force to turn the treatment unit from the operation unit to the treatment unit; an opening and closing force transmission mechanism, provided between the operation unit and the treatment unit along the insertion unit, and transmitting an opening and closing force as a force to open and close the clamping section from the operation unit to the treatment unit; and a common operation mechanism, provided in the operation unit, which can generate the turn force transmitted by the turn force transmission mechanism and which can also generate the opening and closing force transmitted by the opening and closing transmission mechanism.

The surgical instrument in accordance with a second aspect of the present invention comprises: an insertion unit; a treatment unit provided at one end of the insertion unit and capable of executing a plurality of actions; an operation unit provided at the other end of the insertion unit; a first force transmission mechanism, provided between the operation unit and the treatment unit along the insertion unit, and transmitting a first force that causes the treatment unit to execute one prescribed action to the treatment unit from the operation unit; a second force transmission mechanism, provided between the operation unit and the treatment unit along the insertion unit, and transmitting a second force that causes the treatment unit to execute another action that is different from the one action to the treatment unit from the operation unit; and a common operation mechanism, provided in the operation unit, which can generate the first force transmitted by the first force transmission mechanism and which can also generate the second force transmitted by the second force transmission mechanism.

The surgical instrument in accordance with a third aspect of the present invention comprises: an insertion unit; a treatment unit provided at one end of the insertion unit, and comprising a pair of jaws that can be opened and closed and turnable about one axis; an operation unit provided at the other end of the insertion unit; a turn force transmission mechanism, provided between the operation unit and the treatment unit along the insertion unit, and transmitting a turn force as a force to turn the treatment unit from the operation unit; an opening and closing force transmission mechanism, provided between the operation unit and the treatment unit along the insertion unit, and transmitting an opening and closing force as a force to open and close the jaws of the treatment unit from the operation unit; and a control mechanism provided in the operation unit and having a turn force input section which can generate the turn force transmitted by the turn force transmission mechanism and an opening and closing force input section which can generate the opening and closing force transmitted by the opening and closing force transmission mechanism.

The surgical instrument in accordance with a fourth aspect of the present invention comprises: an insertion unit; a treatment unit provided at one end of the insertion unit, capable of turning about one axis, and comprising a clamping section capable of opening and closing action; an operation unit provided at the other end of the insertion unit; turn force transmission means, provided between the operation unit and the treatment unit along the insertion unit, and transmitting a turn force as a force to turn the treatment unit from the operation unit to the treatment unit; opening and closing force transmission means, provided between the operation unit and the treatment unit along the insertion unit, and transmitting an opening and closing force as a force to open and close the clamping section from the operation unit to the treatment unit; and common operation means, provided in the operation unit, which can generate the turn force transmitted by the turn force transmission means and which can also generate the opening and closing force transmitted by the opening and closing transmission means.

The surgical instrument in accordance with a fifth aspect of the present invention comprises: an insertion unit; a treatment unit provided at one end of the insertion unit and capable of executing a plurality of actions; an operation unit provided at the other end of the insertion unit; first force transmission means, provided between the operation unit and the treatment unit along the insertion unit, and transmitting a first force that causes the treatment unit to execute one prescribed action to the treatment unit from the operation unit; second force transmission means, provided between the operation unit and the treatment unit along the insertion unit, and transmitting a second force that causes the treatment unit to execute another action that is different from the one action to the treatment unit from the operation unit; and common operation means, provided in the operation unit, which can generate the first force transmitted by the first force transmission means and which can also generate the second force transmitted by the second force transmission means.

The surgical instrument in accordance with a sixth aspect of the present invention comprises: an insertion unit; a treatment unit provided at one end of the insertion unit, and comprising a pair of jaws that can be opened and closed and turnable about one axis; an operation unit provided at the other end of the insertion unit; turn force transmission means, provided between the operation unit and the treatment unit along the insertion unit, and transmitting a turn force as a force to turn the treatment unit from the operation unit; opening and closing force transmission means, provided between the operation unit and the treatment unit along the insertion unit, and transmitting an opening and closing force as a force to open and close the jaws of the treatment unit from the operation unit; and control means provided in the operation unit and having a turn force input section which can generate the turn force transmitted by the turn force transmission means and an opening and closing force input section which can generate the opening and closing force transmitted by the opening and closing force transmission means.

DESCRIPTION OF THE PREFERRED EMBODIMENTS

The preferred embodiments of the present invention will be described below with reference to the appended drawings.

First Embodiment

Figure 1:
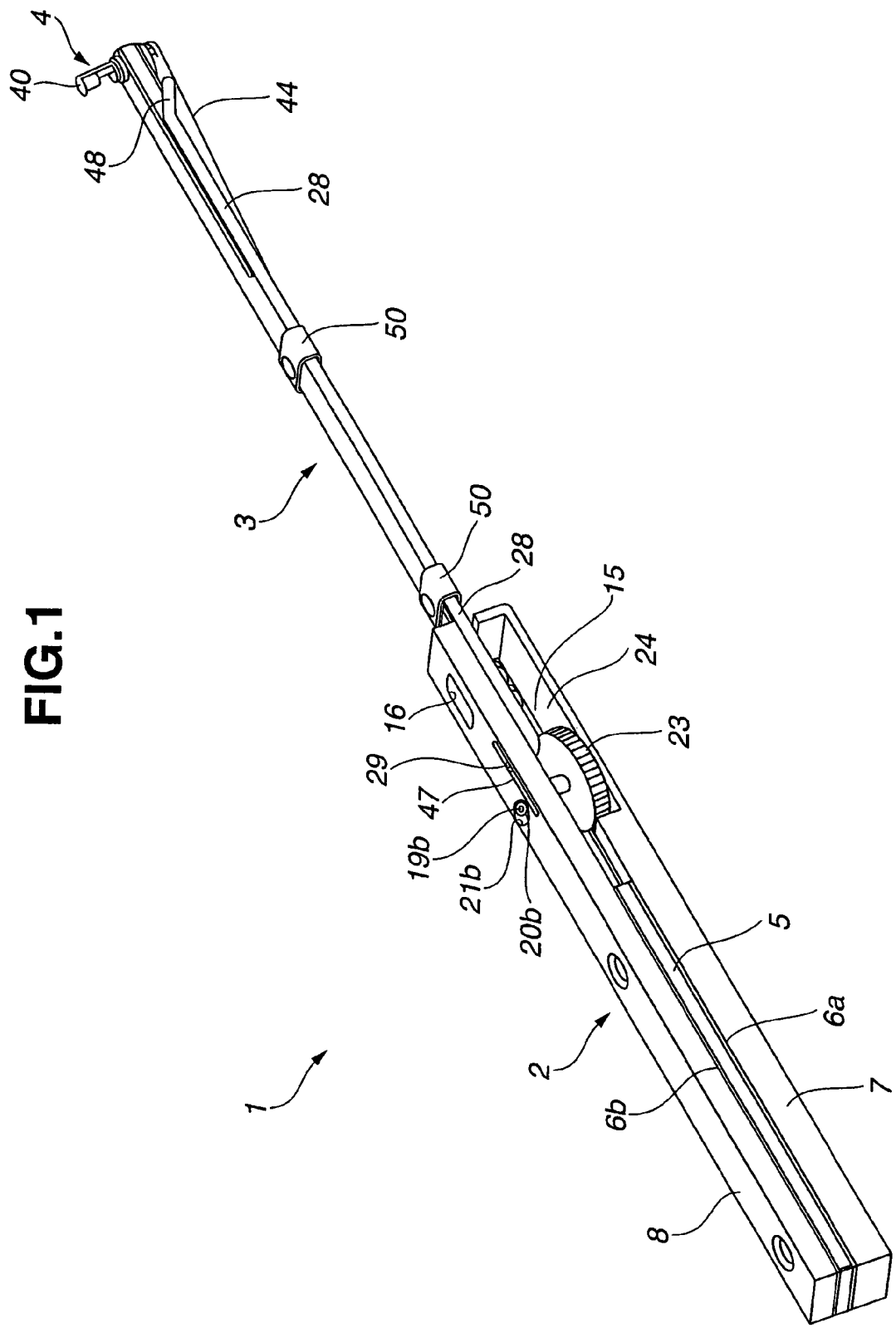
FIG. 1 is a perspective view illustrating the external appearance of the needle driver of a first embodiment of the present invention.
Figure 2:
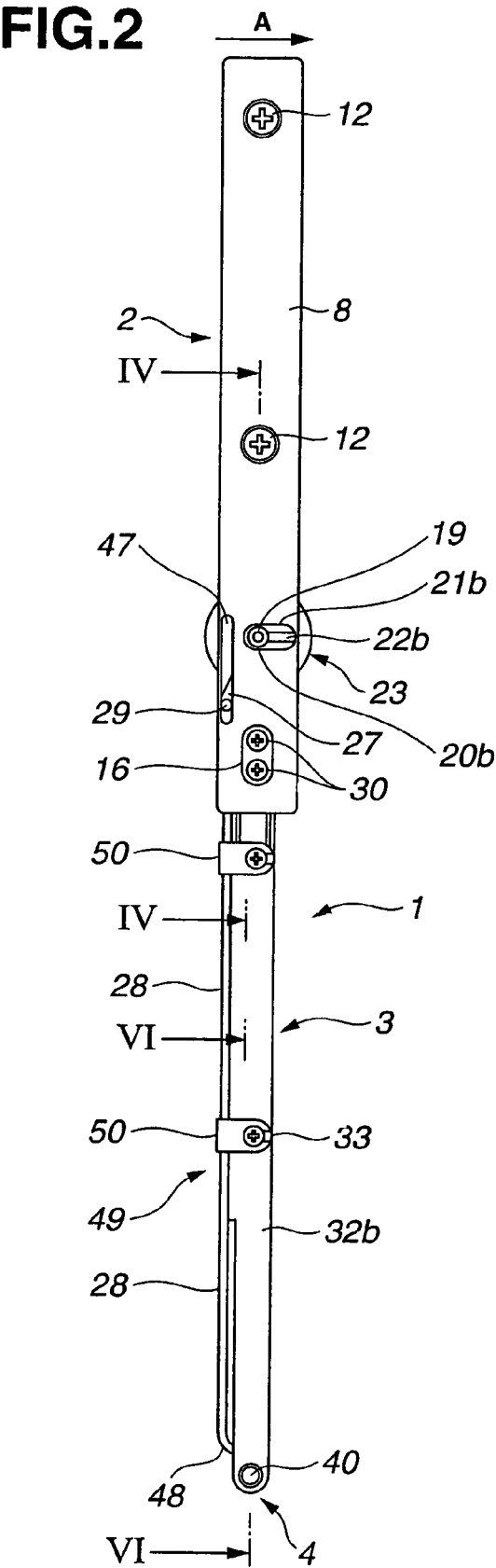
FIG. 2 is a front view of the needle driver of the first embodiment.
Figure 3:
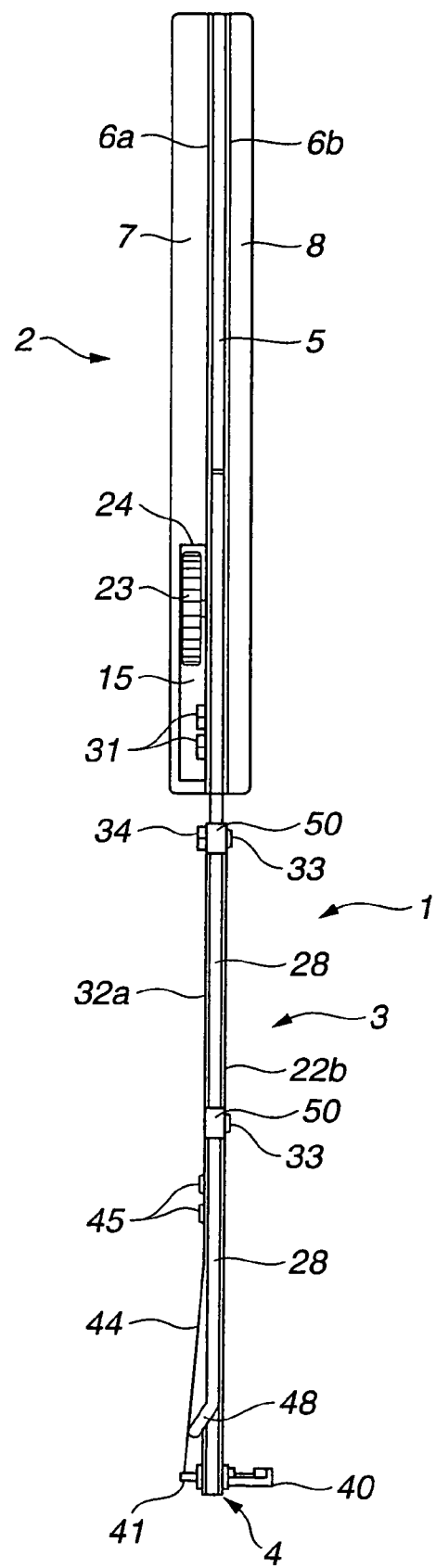
FIG. 3 is a side view of the needle driver of the first embodiment.
Figure 4:
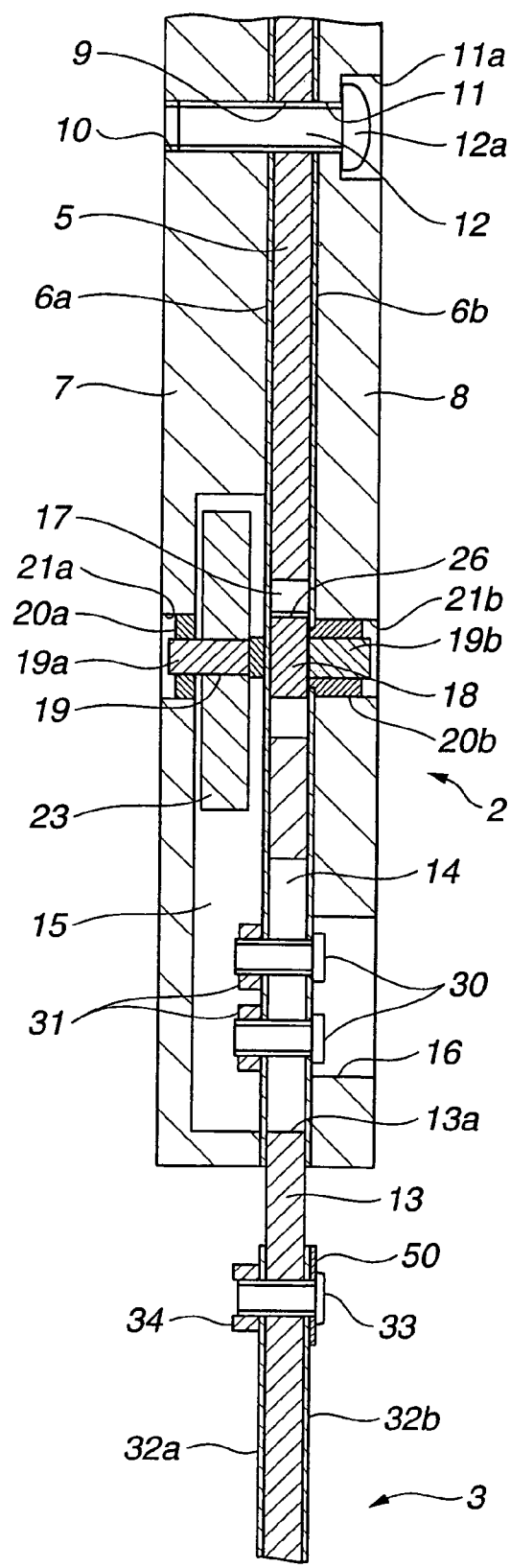
FIG. 4 is a sectional view where the needle driver of the first embodiment is shown as cut by the IV-IV section shown in FIG. 2.
Figure 5:
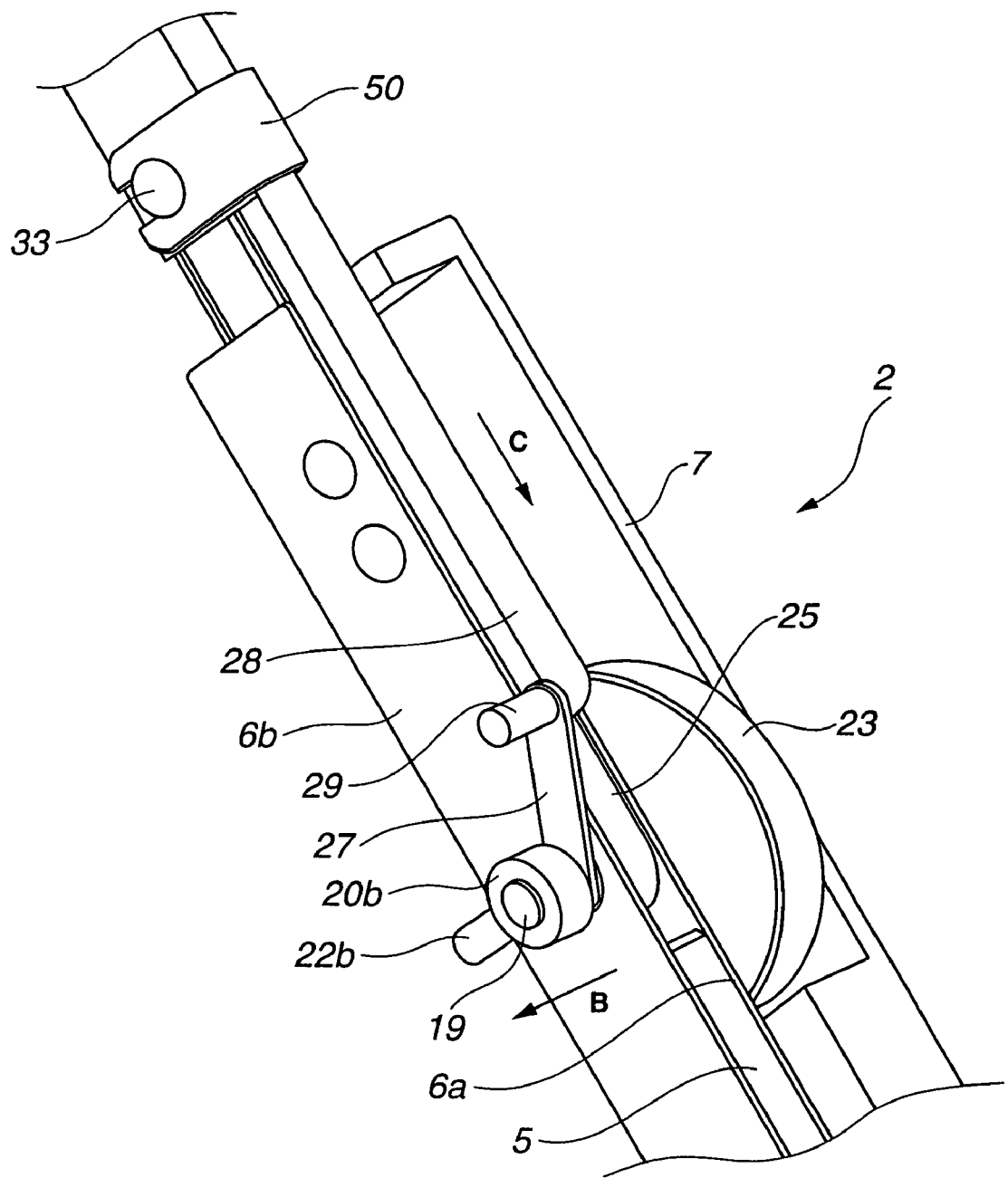
FIG. 5 is a main-part enlarged perspective view illustrating the operation dial, operation dial shaft, and components located in the vicinity thereof in the needle driver of the first embodiment, wherein a portion of the second handle is omitted.

FIG. 1 to FIG. 5 relate to the first embodiment of the present invention. FIG. 1 is a perspective view illustrating the external appearance of the needle driver of the first embodiment of the present invention. FIG. 2 is a front view of the needle driver of the first embodiment. FIG. 3 is a side view of the needle driver of the first embodiment where one side surface thereof is shown. FIG. 4 is a sectional view where the needle driver of the first embodiment is shown as cut by the IV-IV section shown in FIG. 2. FIG. 5 is a main-part enlarged perspective view illustrating the operation dial, operation dial shaft, and components located in the vicinity thereof, wherein a portion of the second handle is omitted.

As shown in FIG. 1 to FIG. 5, a needle driver 1 of the first embodiment comprises as the main components an operation unit 2 that is held with one hand by a surgeon and employed for operation, an insertion unit 3, which is a unit to be inserted into a body to be examined and is provided so as to be linked with one end on the distal end side of the operation unit 2, and a treatment unit 4 provided in an extended condition at the end section of the distal end side of the insertion unit 3 and serving to hold a curved needle for anastomosis.

The configuration of the operation unit 2 will be first explained with reference to FIG. 1 through FIG. 5.

A first fixing plate 5 in the form of a band-like plate body is provided at the proximal end side of the operation unit 2, and sandwiching plates 6a, 6b composed of thin plates made, for example, of a stainless steel are joined respectively to upper and lower surfaces of the first fixing plate 5. Furthermore, a first handle 7 and a second handle 8 are in the form of a band-like plate body and joined via the sandwiching plates 6a, 6b respectively to upper and lower surfaces of the first fixing plate 5.

As shown by a longitudinal sectional side view of the operation unit 2 in FIG. 4, a plurality of through holes 9 are provided in the first fixing plate 5 comprising the sandwiching plates 6a, 6b, those holes being arranged in the lengthwise direction of the fixing plate with a certain spacing therebetween. Furthermore, threaded holes 10 facing the through holes 9 are drilled in the first handle 7, and mounting holes 11 facing the through holes 9 are drilled in the second handle 8. Handle fixing screws 12 are screwed from the mounting holes 11 into the threaded holes 10 via the through holes 9, and the first and second handles 7, 8 are respectively fixed to the first fixing plate 5 from both sides thereof. The mounting hole 11 is provided with a concave section 11a to accommodate a head 12a of the handle fixing screw 12.

At the distal end side of the operation unit 2, a proximal end section of a second fixing plate 13 is provided so as to be freely moveable back and forth in the front-rear direction (long axis direction of the operation unit 2) in a state of being inserted into the first and second handles 7, 8 via the sandwiching plates 6a, 6b. The second fixing plate 13 is in the form of a strip-like plate body that is narrower than the first fixing plate 5, and a long hole 14 extending in the front-rear direction (long axis direction) is provided so as to pass through the proximal end section thereof. Furthermore, a recess 15 is provided in the first handle 7 facing the distal end section of the first fixing plate 5 and the long hole 14 of the second fixing plate 13, and an opening 16 facing the long hole 14 is provided in the second handle 8.

Furthermore, a gap 17 is formed between the distal end surface of the first fixing plate 5 and the proximal end surface of the second fixing plate 13, and an operation pulley 18 is provided in this gap 17. The gap 17 is formed in a location shifted closer to the joint with the insertion unit 3 from the center of the operation unit 2.

An operation dial shaft 19 serving, too, as a shaft of the below-described operation dial 23 is passed through and fixed in the center of the operation pulley 18. A sliding bearing 20a abuts against the end section 19a of the operation dial shaft 19 on the side of the first handle 7, and a sliding bearing 20b abuts against the end section 19b of the operation dial shaft on the side of the second handle 8. The operation dial shaft 19 is turnably supported by those sliding bearings 20a, 20b.

The end section 19a of the operation dial shaft 19 and the sliding bearing 20a are disclosed in the below-described guide long hole 21a formed in the surface of the first handle 7. On the other hand, the end section 19b of the operation dial shaft 19 and the sliding bearing 20b are disclosed in the below-described guide long hole 21b formed in the surface of the second handle 8.

Furthermore, the guide long holes 21a and 21b having the shape of elongated holes are formed in the short axis direction (width direction) from the position, where the sliding bearing 20a and sliding bearing 20b are disclosed, toward one side of the operation unit 2 in the surface of the first handle 7 and surface of the second handle 8.

Furthermore, the sliding bearing 20a is provided so that it can slide along the guide long hole 21a formed in the first handle 7, and the sliding bearing 20b is provided so that it can slide along the guide long hole 21b formed in the second handle 8.

Inside the guide long holes 21a and 21b, impelling springs 22a and 22b are respectively provided between the sliding bearings 20a, 20b and the first handle 7 and the second handle 8. As a result, the sliding bearings 20a and 20b (that is, the shaft end sections 19a and 19b of the operation dial shaft 19) are impelled from one side of the operation unit 2 in the central axis direction by the impelling springs 22a and 22b, respectively.

On the other hand, an operation dial 23 having the operation dial shaft 19 as a shaft is provided in the recess 15 in the first handle 7.

The operation dial shaft 19 is passed through and fixed in the center of the operation dial 23, and the operation dial is provided so that it can move in the direction of short axis (width direction) of the operation unit 2 following the movement of the operation dial shaft 19 and sliding bearings 20a, 20b along the guide long holes 21a, 21b.

The diameter of the operation dial 23 is larger than the width (width in the short axis direction) of the first handle 7, and part of the outer peripheral surface of the operation dial is provided so as to protrude outward from the openings 24 of both side surfaces of the first handle 7 toward both sides thereof. Furthermore, a sliding stopper is provided, for example, by coating with a rubber member or by roulette processing that produces convexes and concaves on the outer peripheral surface of the operation dial 23, and a turn force is transferred via the operation dial shaft 19 to the operation pulley 18 when the operator of the needle driver 1 turns the operation dial 23 with his finger. Furthermore, a belt 25 is stretched over the operation pulley 18.

In the first embodiment, the operation dial 23 and operation pulley 18 turn together integrally via the operation dial shaft 19 that is passed through and fixed to the operation dial 23 and operation pulley 18, but another configuration may be also used in which the operation dial 23 and operation pulley 18 are directly fixedly attached so that the central axis thereof match and are together freely turnably supported with respect to the operation dial shaft 19.

In the sandwiching plates 6a, 6b, two adjustment screws 30 are provided through long holes 14 from the opening 16 side of the second handle 8 and the adjustment screws 30 are tightened with adjustment nuts 31. Therefore, by tightening the adjustment screws 30, it is possible to move the second fixing plate 13 back and forth in the long axis direction (front-rear direction) of the operation unit 2 within the range of the long hole 14 and the tension of the belt 25 can be adjusted at the assembling stage.

Furthermore, sandwiching plates 32a, 32b made of thin plates, for example, of stainless steel are provided respectively at both side surfaces in part of the second fixing plate 13. Those sandwiching plates 32a, 32b are fixed to the second fixing plate 13 with a plurality of plate locking screws 33 and nuts 34. The sandwiching plates 32a, 32b are formed to be somewhat wider than the second fixing plate 13, and belt guiding grooves for preventing the belt 25 from moving in the width direction are provided at both sides of the second fixing plate 13 so as to allow the belt to move back and forth. Therefore, the second fixing plate 13 is formed to have a thickness substantially equal to the width of the belt 25.

The insertion unit 3 and treatment unit 4 will be explained below in greater detail with reference to FIG. 6 through FIG. 9.

Figure 6:
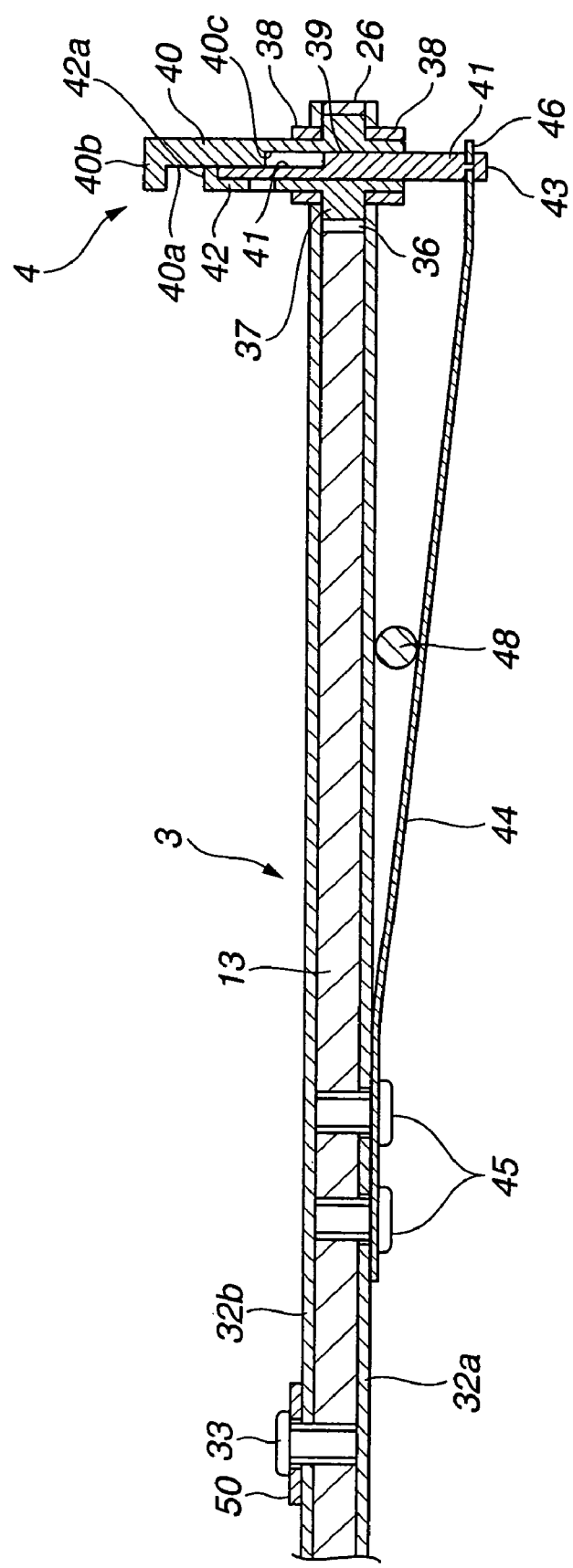
FIG. 6 is a sectional view illustrating the insertion unit and treatment unit in the needle driver of the first embodiment, with the view being obtained by cutting along the section VI-VI shown in FIG. 2 and illustrating the arrangement in a state where the treatment unit is open.
Figure 7:
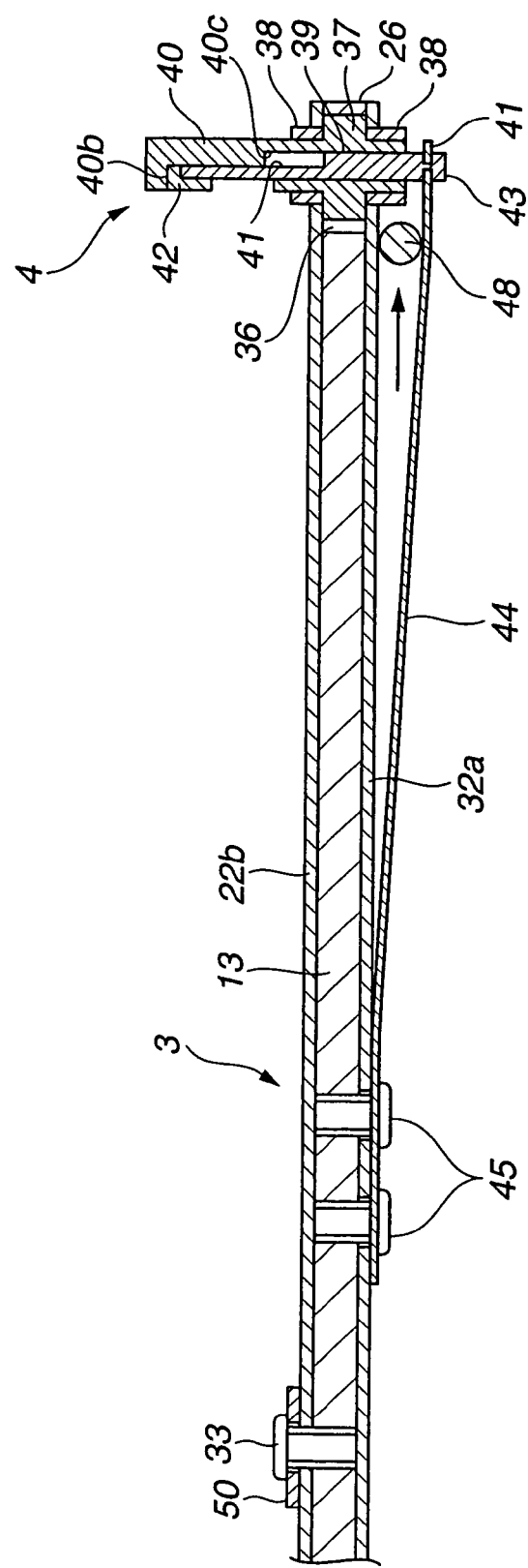
FIG. 7 is a sectional view illustrating the insertion unit and treatment unit in the needle driver of the first embodiment, with the view being obtained by cutting along the section VI-VI shown in FIG. 2 and illustrating the arrangement in a state where the treatment unit is closed.
Figure 8:
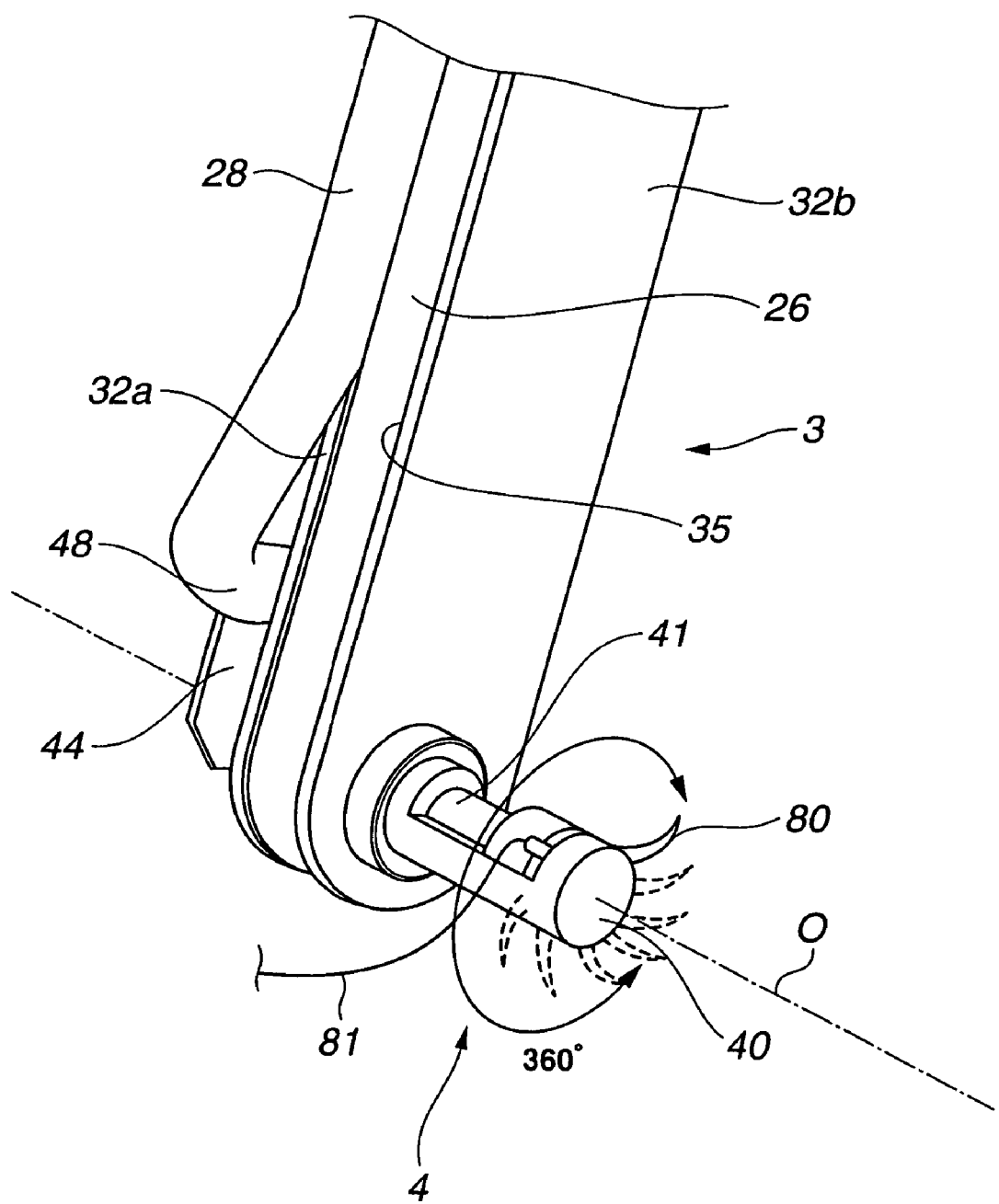
FIG. 8 is a main-part enlarged perspective view showing on an enlarged scale the vicinity of the treatment unit in the needle driver of the first embodiment.
Figure 9:
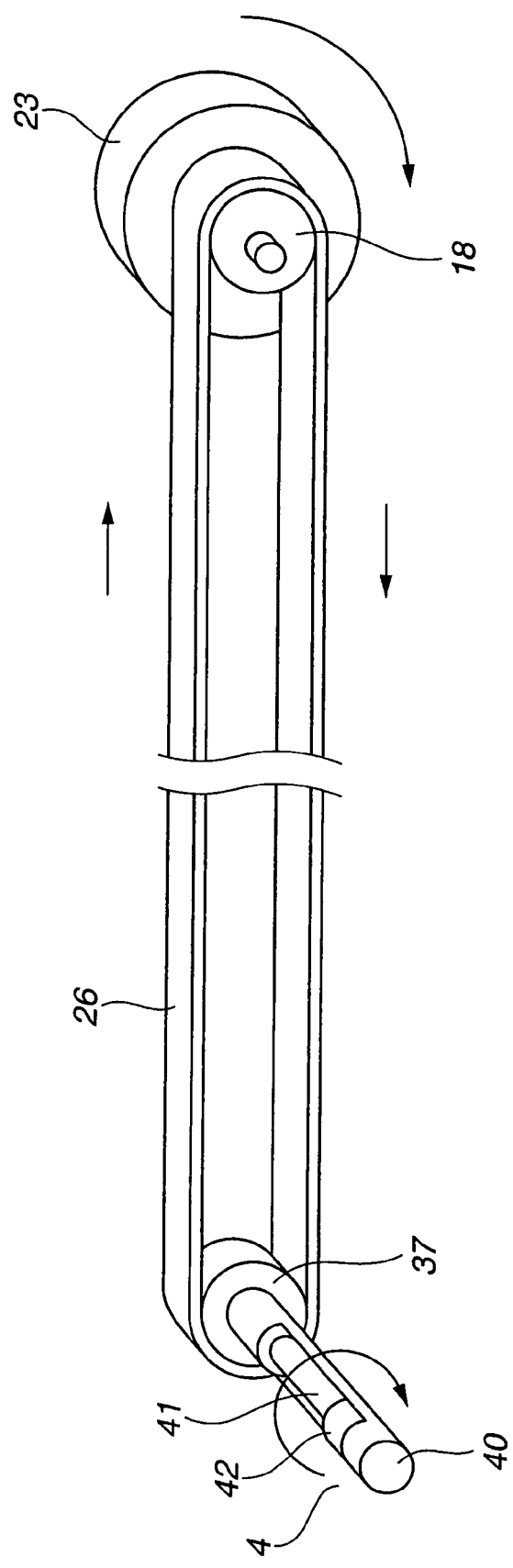
FIG. 9 is a main-part enlarged perspective view illustrating schematically the turn force transfer mechanism of the operation dial in the needle driver of the first embodiment.

FIG. 6 and FIG. 7 are sectional views illustrating the insertion unit and treatment unit in the needle driver of the first embodiment of the present invention, those views being obtained by cutting along the VI-VI section shown in FIG. 2. FIG. 6 illustrates the arrangement in a state where the treatment unit is open, and FIG. 7 illustrates the arrangement in a state where the treatment unit is closed. FIG. 8 is a main-part enlarged perspective view showing on an enlarged scale the vicinity of the treatment unit in the needle driver of the first embodiment. FIG. 9 is a main-part enlarged perspective view illustrating schematically the turn force transfer mechanism of the operation dial in the needle driver of the first embodiment.

As shown in FIG. 6 and FIG. 7, the distal end section of the second fixing plate 13 is formed to be shorter than the sandwiching plates 32a, 32b, and a gap 36 is provided in the distal end section of the second fixing plate 13. A turn pulley 37 is provided in the gap 36. The central axis O of the turn pulley 37 is perpendicular to the insertion unit 3, and both end sections thereof are freely turnably mounted on the sliding bearing 38.

The sliding bearing 38 is fixed to the sandwiching plates 32a, 32b, the belt 25 is stretched over the turn pulley 37, and the turn of the above-described operation pulley 18 is transferred to the turn pulley 37 with the belt 25 (see FIG. 9).

The above-described operation pulley 18, belt 25, and turn pulley 37 constitute a turn force transfer mechanism for transferring the turn force of the operation dial 23 to the first jaw 40 and second jaw 41 of the below-described treatment unit 4 (see FIG. 9).

A through orifice 39 is provided in the central axis O of the turn pulley 37 in the axial direction thereof. Furthermore, a first clamping section 40 (referred to hereinbelow as the first jaw 40) protruding through the sandwiching plate 32b is provided at one end of the turn pulley 37 so that it can turn integrally therewith.

The first jaw 40 has a substantially cylindrical rod shape, and the central axis in the long axis direction thereof protrudes so as to be perpendicular to the long axis of the insertion unit 3. Furthermore, the first jaw can freely turn around the central axis and also can turn integrally with the turn pulley 37.

Furthermore, a flat surface 40a constituting a part of the central axis O of the first jaw 40 and having a semicircular cross section is formed in the substantially central portion in the long axis direction of the first jaw 40. Furthermore, a clamping surface 40b perpendicular to the central axis in the long axis direction of the first jaw 40 is formed in the distal end section of the first jaw 40.

A second clamping section 41 (referred to hereinbelow as the second jaw 41) that can freely move parallel to the central axis of the first jaw 40 passes through the through hole 39 of the turn pulley 37.

The second jaw 41 has a substantially cylindrical rod shape, a clamping piece 42 that can freely move back and forth with respect to the holding surface 40b is fixed to the distal end section of the second jaw, and a clamping surface 42a facing the clamping surface 40b is provided in the holding piece 42. The second jaw 41 can turn integrally with the turn pulley 37.

Notches 40c and 41b provided with steps are provided on the joining surface of the first jaw 40 and second jaw 41, those notches serving as guides for a sliding back and forth with respect to the first jaw 40.

The rear end section of the second jaw 41 passes through the sandwiching plate 32a, and a small-diameter section 43 is formed at the end thereof. A free end of a plate spring 44 made, for example, of stainless steel and serving to impel the clamping surface 42a in the direction of pressing toward the clamping surface 40b is linked to the small-diameter section 43.

The proximal end section of the plate spring 44 is fixed with a plurality of fixing screws via the sandwiching plate 32a to a substantially central section of the second fixing plate 13. Furthermore, a notched section 46 for mounting the small-diameter section 43 of the second jaw 41 is formed in the distal end section of the free end of the plate spring 44.

The mechanism for transferring a force supplied for opening and closing operation of the first jaw 40 and second jaw 41 will be explained below by returning to FIG. 1 to FIG. 5.

As shown in FIG. 1 and FIG. 2, a guide long hole 21b is formed, as described above, in the surface of the second handle 8 from the central axis of the operation unit 2 to one side of the operation unit 2. A guide groove 47 provided so as to extend in the long axis direction of the operation unit 2 is formed in the vicinity of the guide long hole 21b in the location shifted toward the other side of the operation unit 2.

On the other hand, a transmission rod 28 for linking the force associated with the operation of the operation dial 23 in the operation unit 2 with the opening and closing operation of the first jaw 40 and second jaw 41 in the treatment unit 4 is provided along the other side of the insertion unit 3. This transmission rod 28 is formed, for example, of stainless steel, an L-shaped curved section 29 is formed at the end thereof on the side of the operation unit 2 and the distal end section of the curved section 29 is freely slidably engaged with the guide groove 47.

Furthermore, as shown in FIG. 5, a link 27 that is provided so that it can slide between the second handle 8 and sandwiching plate 6b is installed between the curved section 29 and operation dial shaft 19.

The curved section 29 is freely turnably fitted in one end section of the link 27, and the operation dial shaft 19 is freely turnably fitted between the sandwiching plate 6b and sliding bearing 20b in the other end section of the link 27.

As described above, the operation dial shaft 19 can be guided together with the sliding bearing 20b by the guide long hole 21b and can move in the width direction of the operation unit 2. Furthermore, if the operation dial shaft 19 is caused to move against the impelling force of the above-described impelling spring 22b (direction shown by arrow B in FIG. 50, then the transmission rod 28 will move via the link 27 in the direction shown by arrow C in FIG. 5.

Returning to FIG. 1, the transmission rod 28 is provided so as to extend to the vicinity of the treatment unit 4 along the second fixing plate 13 and is supported so that it can move back and forth in the long axis direction of the insertion unit 3. Furthermore, a curved section 48 that is curved into a substantially L-like shape is formed at the end section of the transmission rod 28, on the side of the treatment unit 4.

The curved section 48 is provided so as to be sandwiched between the sandwiching plate 32a and plate spring 44 and serves to transmit the force for elastically deforming the plate spring 44 to open and close the second jaw 41.

The operation dial shaft 19, sliding bearings 20a, 20b, link 27, transmission rod 28, curved section 48, and plate spring 44 constitute an opening and closing force transmission mechanism, which transfers to the second jaw 41 the force that is generated when the operation dial 23 is pressed sidewise.

Sheet-like members 50 bent into a U-like shape are tightened together by a plurality of plate locking screws 33 for fixing the sandwiching plates 32a, 32b to the second fixing plate 13, those sheet-like members 50 holding the transmission rod 28 such that the transmission rod 28 can freely move back and forth in the axial direction.

The operation of the needle driver of the first embodiment will be described below.

As shown in FIG. 1, FIG. 2, and FIG. 5, if the operator presses the operation dial 23 toward one side (direction shown by arrow A in FIG. 2) of the operation unit 2 against the impelling force of the impelling springs 22a, 22b, the operation dial shaft 19 and sliding bearings 20a, 20b slide in the direction shown by arrow A along the guide long holes 21a, 21b against the impelling force of the impelling springs 22a, 22b.

Due to this movement of the operation dial shaft 19, the transmission rod 28 is pulled to the base side of the operation unit 2 via the link 27, and the distal end of the curved section 48, which is the end section of the transmission rod 28, moves toward the proximal end section of the plate spring 44 against the impelling force of the plate spring 44. As a result, the free end section of the plate spring 44 is pressed and moved in the direction of going away from the sandwiching plate 32a.

On the other hand, when no external force is applied to the operation dial 23, the operation dial shaft 19 is held at the central axis via the sliding bearings 20a, 20b by the impelling force of the impelling springs 22a, 22b. As a result, the transmission rod 28 is held in a position closer to the treatment unit 4 via the link 27. That is, the distal end of the curved section 48 is also held by the impelling force of the plate spring 44 in a state where it is positioned on the distal end side of the free end section of the spring. Furthermore, at this time, the plate spring 44 is held by the impelling force in a state where the distal end of the free end section is pulled in the direction of approaching the sandwiching plate 32a.

Thus, in response to the pressing operation of the operation dial 23, the transmission rod 28 moves along the long axis direction of the insertion unit 3. As a result, the free end section of the plate spring 44 swings via the movement of the curved section 48. Furthermore, following the swinging motion of the free end section of the plate spring 44, the second jaw 41 moves with respect to the first jaw 40 and an opening and closing operation by the clamping surface 40b and clamping surface 42b is implemented.

This operation will be explained below from the standpoint of an operator (surgeon).

The operator holds the operation unit 2 with one hand and presses the operation dial 23 in the width direction of the operation unit 2 with an index finger. As a result, the transmission rod 28 that is in an initial state is pulled toward the base side of the operation unit 2, the free end section of the plate spring 44 swings in the direction of going away from the sandwiching plate 32a, the second jaw 41 is impelled toward the end back side, and the clamping surface 40b and clamping surface 42b assume an open state (the state shown in FIG. 6).

Conversely, if the operator releases the pressing pressure applied to the operation dial 23, the transmission rod 28 that is pulled to the base side of the operation unit 2 returns to the initial state, the free end section of the plate spring 44 swings in the direction of coming up to the sandwiching plate 32a, the second jaw 41 is pressed toward the front end side and the clamping surface 40b and clamping surface 42b assume a closed state (the state shown in FIG. 7).

Figure 10:
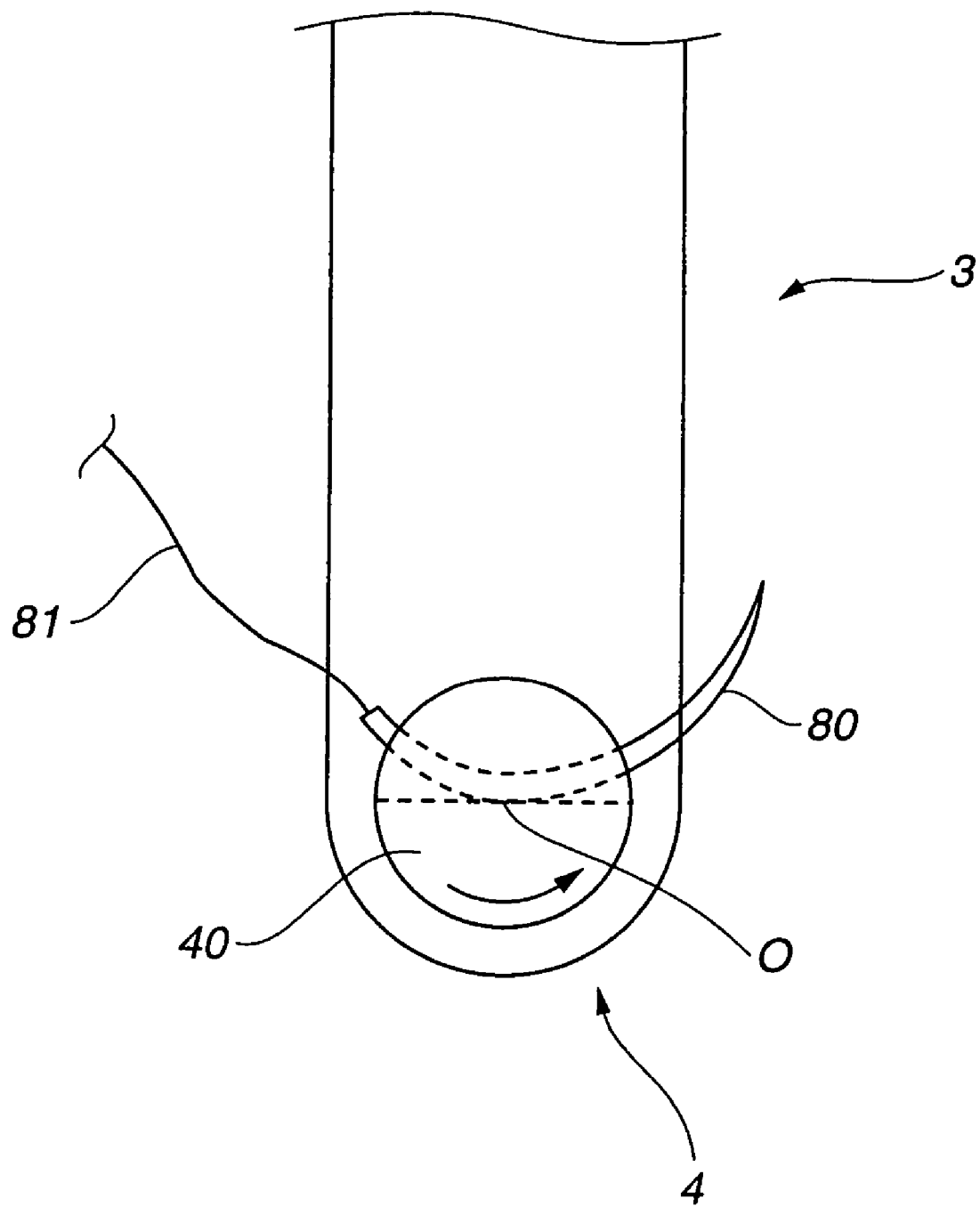
FIG. 10 is a main-part enlarged view illustrating the distal end section of the treatment unit in the needle driver of the first embodiment.

Thus, by pressing and releasing the operation dial 23, the surgeon can clamp a curved needle 80 for anastomosis that has a circular arc shape between the clamping surface 40b and clamping surface 42b in the first jaw 40 and second jaw 41 (see FIG. 8 and FIG. 10).

Furthermore, because the clamping surface 42b and clamping surface 40a are maintained in a closed state of being in contact with each other by the impelling force of the plate spring 44, even if the finger is removed from the operation dial 23, the curved needle 80 for anastomosis is prevented form being inadvertently dropped.

On the other hand, if the surgeon turns the operation dial 23 with the index finger, then the operation pulley 18 that turns integrally with the operation dial 23 is turned and the turn pulley 37 located on the side of the treatment unit 4 is turned via the belt 25. As a result, the first jaw 40 and second jaw 41 turn and the curved needle 80 for anastomosis that is held between the clamping surface 40b and clamping surface 42b turns as shown in FIG. 8 and FIG. 10. That is, the surgeon can conduct the treatment such as anastomosis by turning the operation dial 23 and using the curved needle 80 for anastomosis clamped in the treatment unit 4.

Furthermore, as shown in FIG. 8 and FIG. 10, the curved needle 80 for anastomosis is curved to a circular arc shape, a tip section is provided at one end thereof, and an eye of the needle is provided at the other end thereof. A stitching thread 81 is connected to the eye of the needle. Furthermore, when the curved needle 80 for anastomosis is held by the clamping surfaces 40b, 42a of the first jaw 40 and second jaw 41, the needle is clamped parallel to the circular arc direction of the curved needle 80 for anastomosis. Moreover, a convex circular arc section of the curved needle 80 for anastomosis is clamped in a state of contact with the flat surface 40a of the first jaw 40. In other words, the curved needle 80 for anastomosis is held in a position of in the vicinity of the central axis O of the first jaw 40. As a result, when the first jaw 40 and second jaw 41 turn about the central axis O, the curved needle 80 for anastomosis turns substantially about the central axis O of the first jaw 40.

Thus, with the needle driver of the first embodiment, the surgeon can perform the operations of opening and closing and turning the treatment unit that clamps and turns the curved needle for anastomosis by operations only with prescribed one finger. Thus, two operations, that is, the turn operation and opening and closing operation of the treatment unit can be conducted with a single finger, the operations are simple and the finger operating the operation dial 23 may act independently even in the course of operating the treatment unit 4. Therefore, the operation unit 2 can be clamped with good stability, the positioning of the distal end of the curved needle 80 for anastomosis clamped by the treatment unit 4 is facilitated, the needle can be moved accurately, and anastomosis quality during surgery can be improved. Furthermore, because the operations are facilitated, the surgery time is shortened, the burden on the patient is reduced, the stay period of the patient in the hospital is shortened, the patient can be rapidly returned to society, the turnaround efficiency of beds for hospitalized patients is increased, and the effective hospital management can be realized.

Furthermore, in the first embodiment, the explanation is conducted with respect to an index finger of one hand of the surgeon as the prescribed single finger, but it goes without saying that this example is not limiting.

Second Embodiment

The second embodiment of the present invention will be described below.

Figure 11:
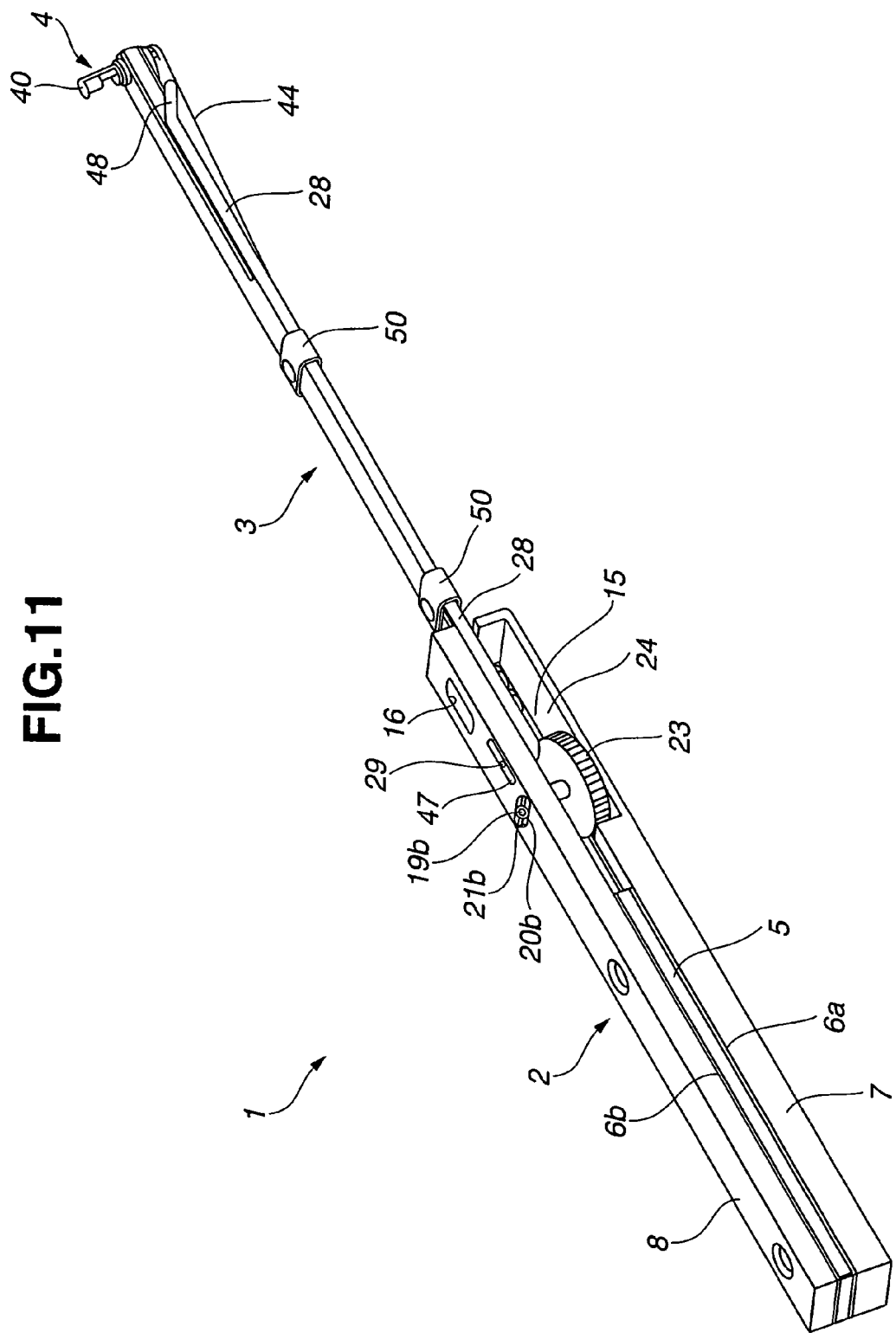
FIG. 11 is a perspective view illustrating the external appearance of the needle driver of a second embodiment of the present invention.
Figure 12:
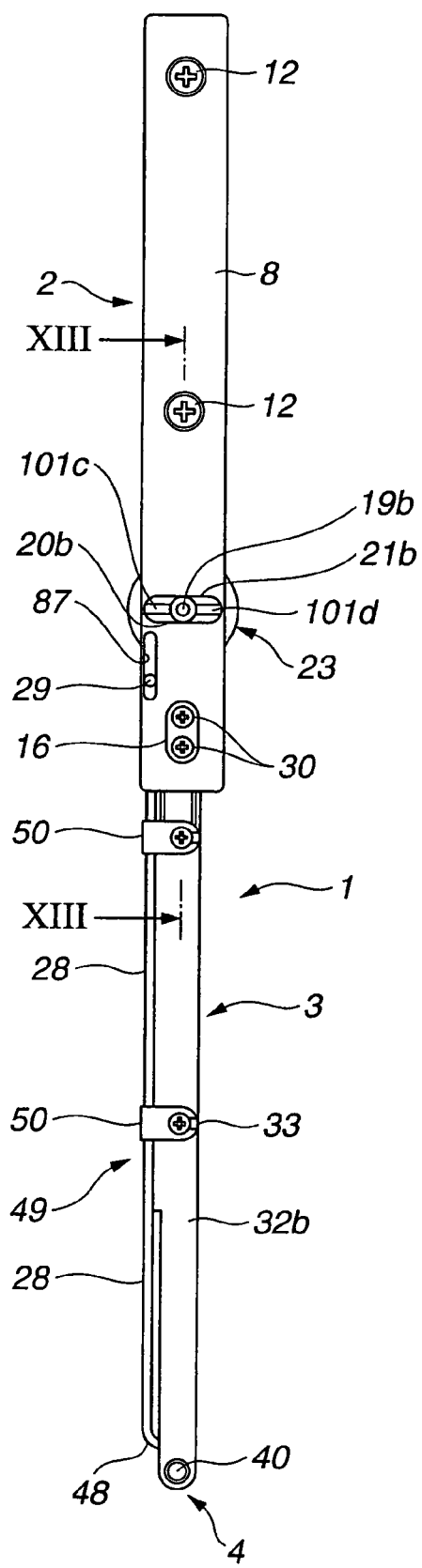
FIG. 12 is a front view of the needle driver of the second embodiment.
Figure 13:
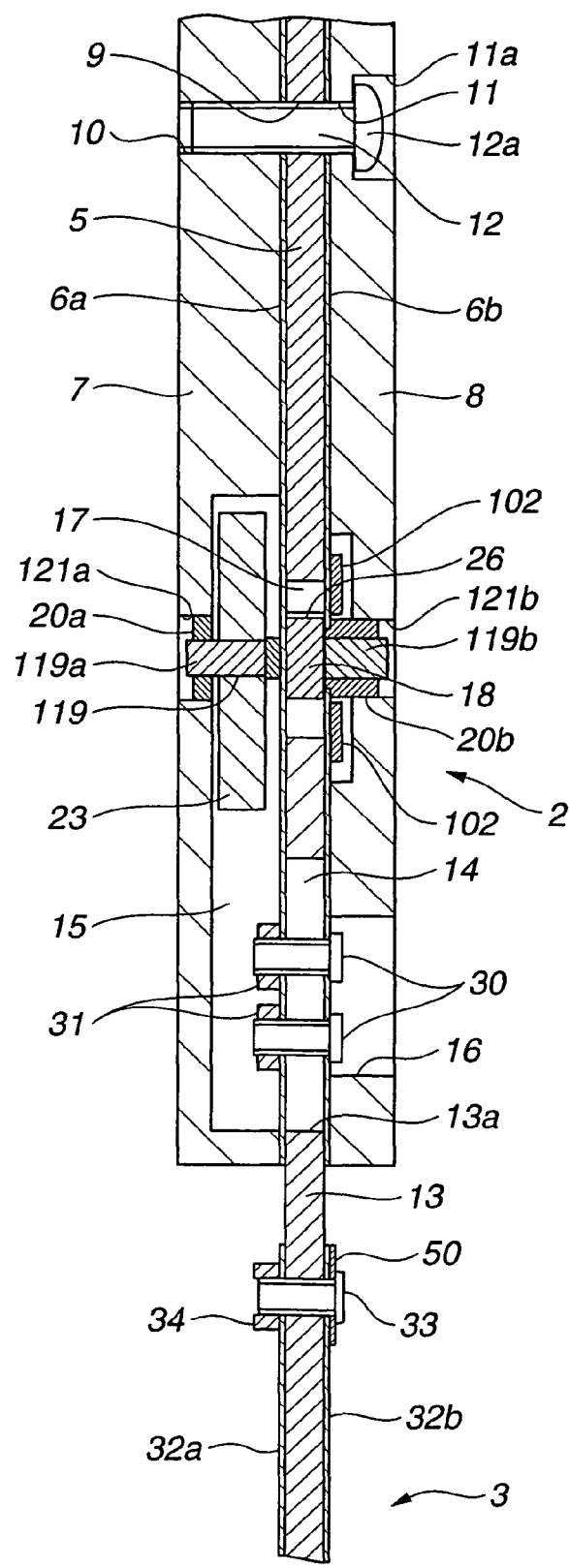
FIG. 13 is a sectional view where the needle driver of the second embodiment is shown as cut by the XIII-XIII section shown in FIG. 12.
Figure 14:
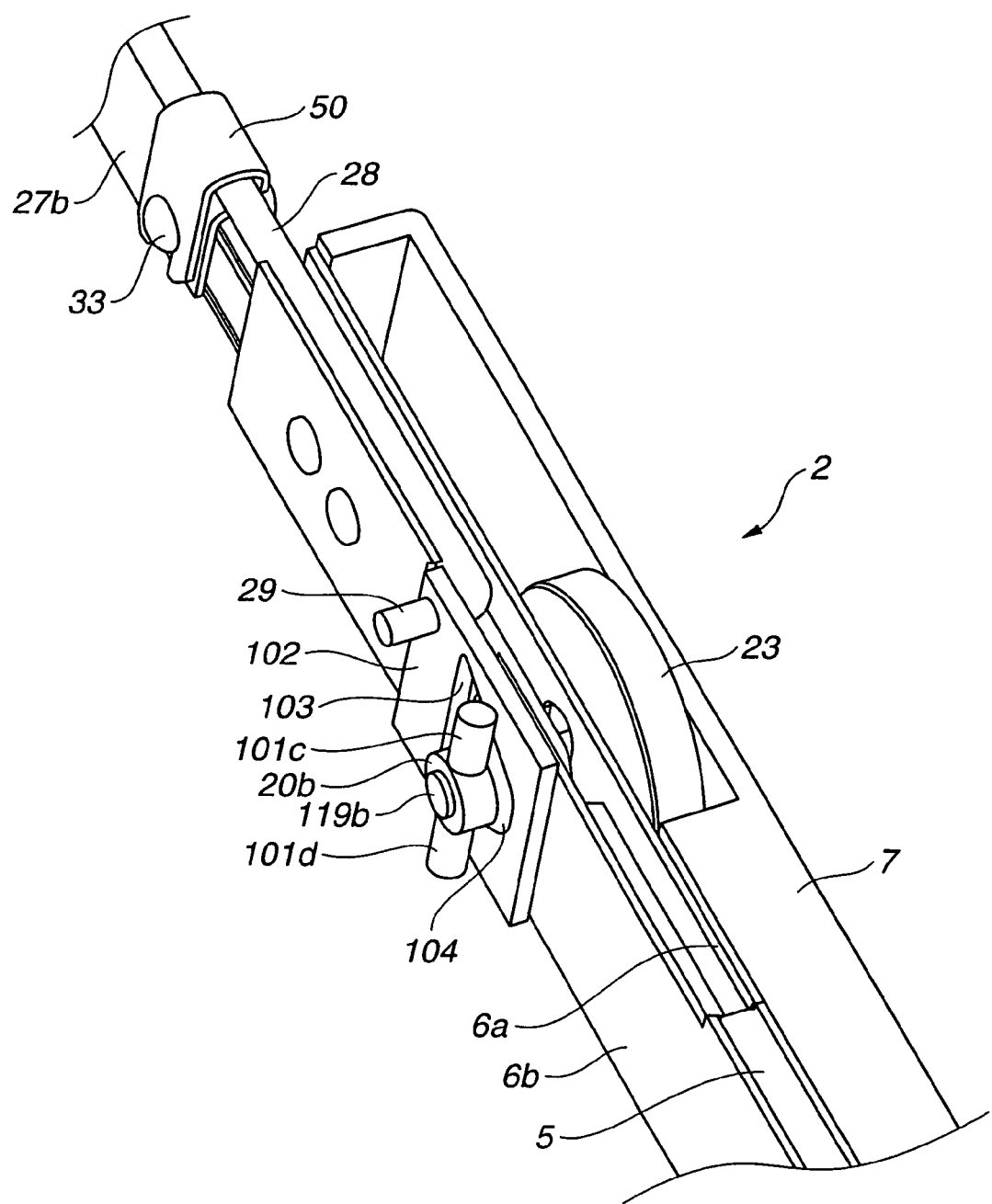
FIG. 14 is a main-part enlarged perspective view illustrating the operation dial, operation dial shaft, and components located in the vicinity thereof in the needle driver of the second embodiment, wherein a portion of the second handle is omitted.

FIG. 11 through FIG. 14 relate to the second embodiment of the present invention. FIG. 11 is a perspective view illustrating the external appearance of the needle driver of the second embodiment of the present invention. FIG. 12 is a front view of the needle driver of the second embodiment. FIG. 13 is a sectional view where the needle driver of the second embodiment is shown as cut by the XIII-XIII section shown in FIG. 12. FIG. 14 is a main-part enlarged perspective view illustrating the operation dial, operation dial shaft, and components located in the vicinity thereof in the needle driver of the second embodiment, wherein a portion of the second handle is omitted.

Because the basic structure of the needle driver of the second embodiment is identical to that of the first embodiment, only the difference therebetween will be explained and the explanation of identical components will be omitted.

As shown in FIG. 11 through FIG. 14, the needle driver 1A of the second embodiment differs from the needle driver of the first embodiment only by the configuration of the operation unit 2. The insertion unit 3 and treatment unit 4 are identical to those of the first embodiment.

The difference between the configuration of the operation unit 2A of the second embodiment and that of the operation unit 2 of the first embodiment described above will be explained hereinbelow with reference to FIG. 1 through FIG. 5.

Similarly to the operation unit 2, the operation unit 2A is provided with a first fixing plate 5, sandwiching plates 6a, 6b, first handle 7, and second handle 8.

Furthermore, a gap 17 is formed between the distal end surface of the first fixing plate 5 and the proximal end surface of the second fixing plate 13, an operation pulley 18 is provided in this gap 17, and an operation dial shaft 119 serving, too, as a shaft of the below-described operation dial 23 is passed through and fixed in the center of the operation pulley 18. A sliding bearing 20a abuts against the end section 119a of the operation dial shaft 119 on the side of the first handle 7, and a sliding bearing 20b abuts against the end section 119b on the side of the second handle 8. The operation dial shaft 119 is freely turnably supported by those sliding bearings 20a, 20b.

The end section 119a of the operation dial shaft 119 and the sliding bearing 20a are disclosed in the below-described guide long hole 121a formed in the surface of the first handle 7. On the other hand, the end section 119b of the operation dial shaft 119 and the sliding bearing 20b are disclosed in the below-described guide long hole 121b formed in the surface of the second handle 8.

In the second embodiment, the guide long holes 121a and 121b, each having the shape of elongated hole, are formed in the short axis directions (width direction) toward both sides of the operation unit 2A from the position where the sliding bearing 20a and sliding bearing 20b are disclosed at the surface of the first handle 7 and the surface of the second handle 8.

Furthermore, the sliding bearing 20a is provided so that that it can slide along the guide long hole 121a formed in the first handle 7, and the sliding bearing 20b is provided so that it can slide along the guide long hole 121b formed in the second handle 8.

Inside the guide long holes 121a and 121b, impelling springs 101a, 101b and 101c, 101d are provided between sliding bearings 20a, 20b and the inner wall surfaces on both sides of the first handle 7 and second handle 8, respectively (in particular, the impelling springs inside the guide long hole 121b are denoted by reference symbols 101c, 101d as shown in FIG. 12 and FIG. 14). As a result, the sliding bearings 20a and 20b (that is, the shafts 119a and 119b of the operation dial shaft 119) are together impelled from both sides of the operation unit 2A in the central axis direction by two impelling springs.

As a result, the sliding bearings 20a, 20b are supported by the respective impelling springs and held in the central section of the respective guide long holes 121a, 121b in a state where no external force is applied.

On the other hand, the operation dial 23 having the operation dial shaft 119 as an axis is provided in the recess 15 formed in the first handle 7.

The operation dial shaft 119 is passed through and fixed to the center of the operation dial 23, and the operation dial 23 is provided so that it can move in the short axis direction (width direction) of the operation unit 2A, following the movement of the operation dial shaft 119 and sliding bearings 20a, 20b along the guide long holes 121a, 121b.

In the second embodiment, too, the diameter of the operation dial 23 is larger than the width (width in the short axis direction) of the first handle 7, part of the outer peripheral surface of the operation dial protrudes outward to both sides from the openings 24 in both end surfaces of the first handle 7, a sliding stopper is provided by roulette processing or the like on the outer peripheral surface, and the operation dial 23 is turned by a finger of the operator of the needle driver 1A, thereby transmitting the turn force to the operation pulley 18 via the operation dial shaft 119. Furthermore, the belt 25 is stretched over the operation pulley 18.

A mechanism for transmitting the force providing for opening and closing operation of the treatment unit 4 in the second embodiment will be explained below.

As shown in FIG. 11 and FIG. 12, the guide long hole 121b is formed, as described above, from the central axis of the operation unit 2A toward both sides of the operation unit 2A in the surface of the second handle 8, and a guide groove 87 extending in the long axis direction of the operation unit 2A is formed in a position shifted toward the other side of the operation unit 2A in the vicinity of the guide long hole 121b.

On the other hand, a transmission rod 28 (similar to that of the first embodiment) for linking the force associated with the operation of the operation dial 23 in the operation unit 2A with the opening and closing operation of the first jaw 40 and second jaw 41 (see the first embodiment) in the treatment unit 4 is provided along the other side of the insertion unit 3.

In the transmission rod 28, an L-shaped curved section 29 is formed at the end thereof on the side of the operation unit 2A, and the distal end section of the curved section 29 is freely slidably engaged with the guide groove 87.

Furthermore, as shown in FIG. 14, a drive direction conversion plate 102 provided slidably between the second handle 8 and sandwiching plate 6b is provided between the curved section 29 and operation dial shaft 119.

A through hole 103 in the form of an equilateral trapezoid having formed therein a cam follower surface of the prescribed slanted surface shape is formed in the central section of the drive direction conversion plate 102. A trapezoidal bearing 104 having as the outer peripheral surface (cam surface) thereof the equilateral trapezoidal shape obtained by cutting the lower bottom side from the aforementioned equilateral trapezoidal shape of the through hole 103 and serving as a bearing member for the operation dial shaft 119 between the sliding bearing 20b and sandwiching plate 6b is provided inside the through hole 103 and slidably come into contact with the cam follower surface in the through hole 103.

The curved section 29 is fitted in one end section of the drive direction conversion plate 102 and driven in the long axis direction of the operation unit 2A by the movement of the drive direction conversion plate 102.

The operation of the needle driver of the second embodiment will be described below.

As shown in FIG. 11, FIG. 12, and FIG. 14, if the operator presses the operation dial 23 toward any one side of the operation unit 2A against the impelling force of the impelling springs 101a, 101b and 101c, 101d, the operation dial shaft 119 and sliding bearings 20a, 20b slide in the corresponding one direction along the guide long holes 121a, 121b against the impelling force of the impelling springs 101a, 101b and 101c, 101d.

Due to the movement of the operation dial shaft 119, the transmission rod 28 is pulled toward the base side of the operation unit 2A via the drive direction conversion plate 102. That is, the slanted surface (cam surface) of the trapezoidal bearing 104 presses the slanted surface (cam follower surface) of the through hole 103, and the drive direction conversion plate 102 moves in parallel toward the base side of the operation unit 2A. Therefore, the transmission rod 28 connected to the drive direction conversion plate 102 via the curved section 29 is pulled toward the base side, and the distal end of the curved section 48, which is the end section of the transmission rod 28, moves toward the proximal end section of the plate spring 44 against the impelling force of the plate spring 44. As a result, the free end section of the plate spring 44 is pressed and moved in the direction of going away from the sandwiching plate 32a.

On the other hand, when no external force is applied to the operation dial 23, the operation dial shaft 119 is held on the central axis via the sliding bearings 20a, 20b by the impelling force of the impelling springs 101a, 101b and 101c, 101d. As a result, the transmission rod 28 is held in a position closer to the treatment unit 4 via the drive direction conversion plate 102. That is, the distal end of the curved section 48 is held in a state positioned on the distal end side of the free end section of the spring by the impelling force of the plate spring 44. Furthermore, at this time, the plate spring 44 is held in a state where the distal end of the free end section thereof is pulled in the direction of approaching the sandwiching plate 32a by the impelling force of the spring.

Thus, similarly to the first embodiment, the transmission rod 28 moves in the long axis direction of the insertion unit 3, following the operation of pressing the operation dial 23, and this movement causes swinging movement of the free end section of the plate spring 44 via the movement of the curved section 48. Furthermore, following the swinging movement of the free end section of the plate spring 44, the second jaw 41 moves with respect to the first jaw 40 and the opening and closing action of the clamping surface 40b and clamping surface 42b is realized.

The turn action of the treatment unit 4 is identical to that of the first embodiment and the explanation thereof is herein omitted.

Thus, with the needle driver of the second embodiment, similarly to the first embodiment, the surgeon can perform the operations of opening and closing and turning the treatment unit that clamps and turns the curved needle for anastomosis by operations only with prescribed one finger. Thus, two operations, that is, the turn operation and opening and closing operation of the treatment unit can be conducted with a single finger, the operations are simple and the finger operating the operation dial 23 may act independently even in the course of operating the treatment unit 4. Therefore, the operation unit 2A can be clamped with good stability, positioning of the distal end of the curved needle 80 for anastomosis clamped by the treatment unit 4 is facilitated, the needle can be moved accurately, and anastomosis quality during surgery can be improved.

Furthermore, because the pressing operation of the operation dial 23 can be performed from both sides of the operation unit, it is possible to adapt to various clamping modes of the operation unit 2.

Thus, in the second embodiment, because the operations are facilitated, the surgery time is shortened, burden on the patient is reduced, the stay period of the patient in the hospital is shortened, the patient can be rapidly returned to society, the turnaround efficiency of beds for hospitalized patients is increased, and effective hospital management can be realized.

Third Embodiment

The third embodiment of the present invention will be described below.

Figure 15:
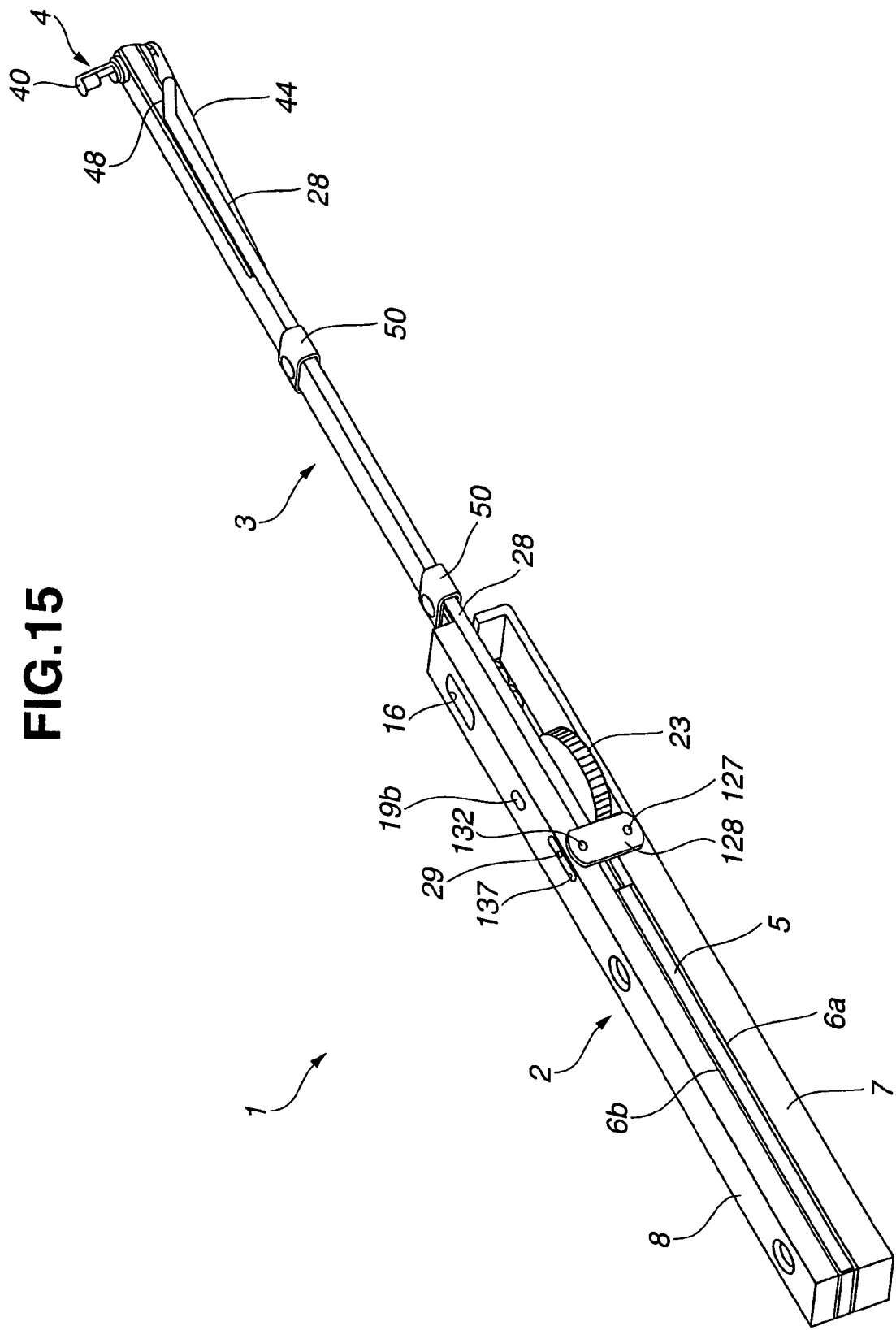
FIG. 15 is a perspective view illustrating the external appearance of the needle driver of a third embodiment of the present invention.
Figure 16:
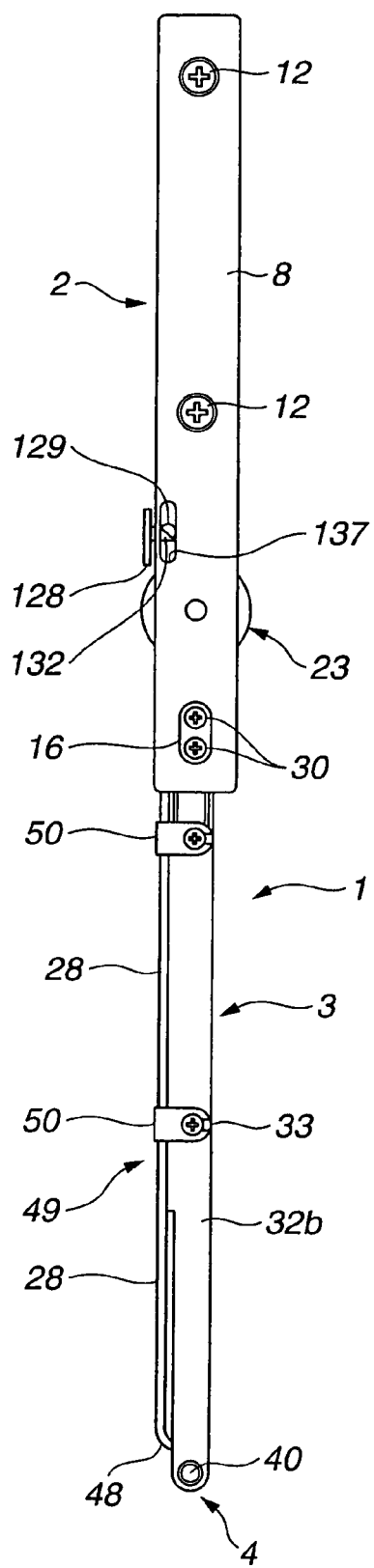
FIG. 16 is a front view of the needle driver of the third embodiment.
Figure 17:
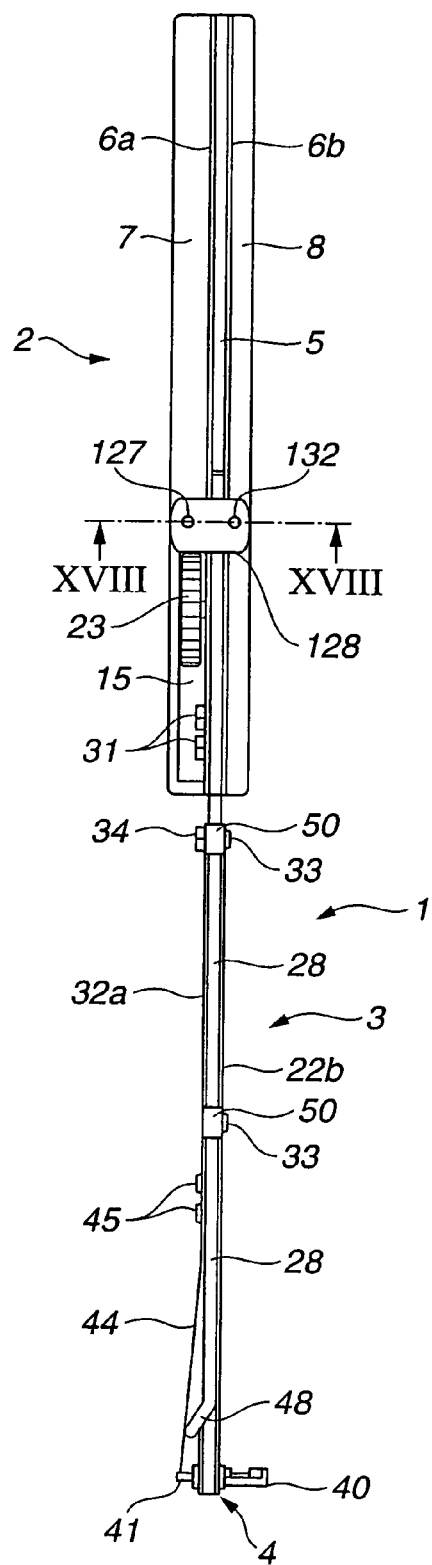
FIG. 17 is a side view of the needle driver of the third embodiment where one side surface thereof is shown.
Figure 18:
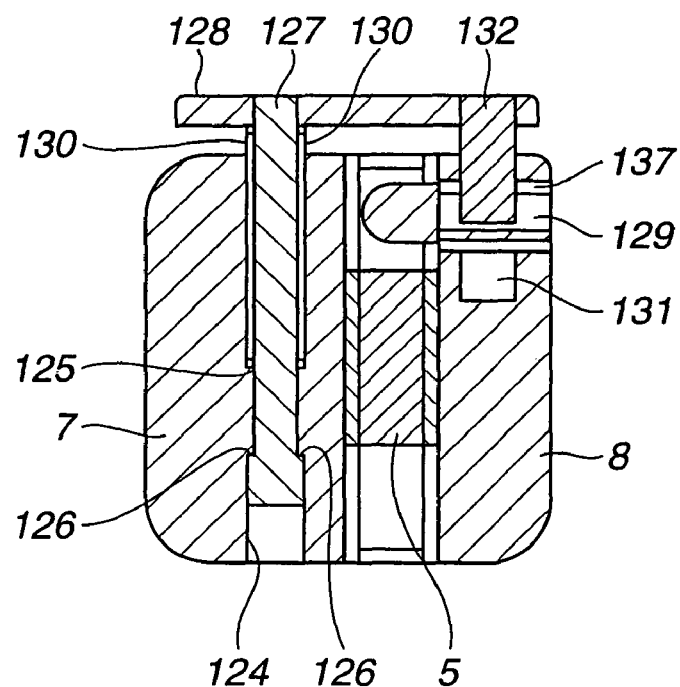
FIG. 18 is a sectional view where the needle driver of the third embodiment is shown as cut by the XVIII-XVIII section shown in FIG. 17.
Figure 19:
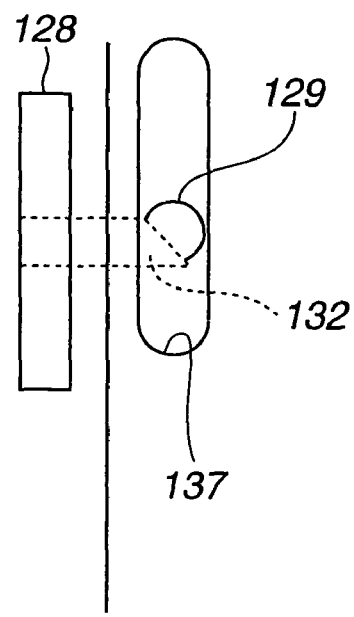
FIG. 19 is a main-part enlarged perspective view illustrating the pressing plate for an opening and closing drive and components located in the vicinity thereof in the needle driver of the third embodiment.

FIG. 15 through FIG. 20 relate to the third embodiment of the present invention. FIG. 15 is a perspective view illustrating the external appearance of the needle driver of the third embodiment of the present invention. FIG. 16 is a front view of the needle driver of the third embodiment. FIG. 17 is a side view of the needle driver of the third embodiment where one side surface thereof is shown. FIG. 18 is a sectional view where the needle driver of the third embodiment is shown as cut by the XVIII-XVIII section shown in FIG. 17. FIG. 19 is a main-part enlarged perspective view illustrating the pressing plate for an opening and closing drive and components located in the vicinity thereof in the needle driver of the third embodiment.

Because the basic structure of the needle driver of the third embodiment is identical to that of the first and second embodiments, only the difference therebetween will be explained and the explanation of identical components will be omitted.

As shown in FIG. 15 through FIG. 19, the needle driver 1B of the third embodiment differs from the needle driver of the first embodiment only by the configuration of the operation unit 2B. The insertion unit 3 and treatment unit 4 are identical to those of the first embodiment.

The difference between the configuration of the operation unit 2B of the third embodiment and that of the operation unit 2 of the first embodiment described above will be explained hereinbelow with reference to FIG. 15 through FIG. 19.

Similarly to the operation unit 2, the operation unit 2B is provided with a first fixing plate 5, sandwiching plates 6a, 6b, first handle 7, and second handle 8.

Furthermore, a gap 17 is formed between the distal end surface of the first fixing plate 5 and the proximal end surface of the second fixing plate 13, an operation pulley 18 is provided in this gap 17, and an operation dial shaft 19 serving, too, as a shaft of the below-described operation dial 23 is passed through and fixed in the center of the operation pulley 18. A sliding bearing 20a abuts against the end section 19a of the operation dial shaft 19 on the side of the first handle 7, and a sliding bearing 20b abuts against the end section 19b on the side of the second handle 8. The operation dial shaft 19 is freely turnably supported by those sliding bearings 20a, 20b.

In the third embodiment, in a similar manner to the above-mentioned embodiments, the diameter of the operation dial 23 is larger than the width (width in the short axis direction) of the first handle 7, part of the outer peripheral surface of the operation dial protrudes outward from the openings 24 in both end surfaces of the first handle 7 to both sides, a sliding stopper is provided by roulette processing or the like on the outer peripheral surface, and the operation dial 23 is turned by a finger of the operator of the needle driver 1B, thereby transmitting the turn force to the operation pulley 18 via the operation dial shaft 19. Furthermore, the belt 25 is stretched over the operation pulley 18.

A mechanism for transmitting the force providing for opening and closing operation of the treatment unit 4 in the second embodiment will be explained below.

As shown in FIG. 15 through FIG. 17, a pressing plate 128 for opening and closing drive of the treatment unit 4 is provided at one side of the operation unit 2B, being a little shifted from the operation dial 23 toward the base side of the operation unit 2B.

Furthermore, a guide groove 137 extending in the long axis direction of the operation unit 2B is formed in the vicinity of the pressing plate 128 in the surface of the second handle 8.

On the other hand, a transmission rod 28 (similar to that of the first embodiment) for linking the force associated with the operation of the pressing plate 128 in the operation unit 2B with the opening and closing operation of the first jaw 40 and second jaw 41 (see the first embodiment) in the treatment unit 4 is provided along the other side of the insertion unit 3. In the transmission rod 28, an L-shaped curved section 129 is formed at the end thereof on the side of the operation unit 2B, and the distal end of the curved section 129 is freely slidably engaged with the guide groove 137.

In the third embodiment, a notch is formed in the axial direction of the curved section 129 so as to form a slanted surface 133 with respect to the long axis direction of the operation unit 2B, as shown in the main-part enlarged section in FIG. 19, in the distal end of the curved section 129.

The engagement relationship of the pressing plate 128 and curved section 129 will be described below.

As shown in FIG. 18, a through hole 124 is provided on the end back side from the operation dial 23 on the first handle 7, and small-diameter locking sections 126 are respectively formed at both sides of the through hole 124. An engagement pin 127 is slidably inserted into the through hole 124, one end of the engagement pin 127 is formed to have a large diameter, and the movement thereof is controlled by the locking section 126. The other end of the engagement pin 127 is mated with and fixed in a through hole formed in the pressing plate 128. Furthermore, an impelling spring 130 is wound around the engagement pin 127. The impelling spring 130 is provided between the locking section 125 and the pressing plate 128, and the pressing plate 128 is impelled thereby in the direction of going away from the first handle 7.

On the other hand, the slanted surface 133 is formed, as described above, at the distal end of the curved section 129 and slidably inserted into the guide groove 137. An orifice 131 is provided in the same direction as the through hole 124 in the guide groove 137. In the orifice 131, a drive pin 132 having formed thereon a slanted surface cut at substantially the same angle as the slanted surface 133 is inserted in the position facing the slanted surface 133 of the curved section 129. Furthermore, the other end of the drive pin 132 is mated with and fixed in the through hole formed in the pressing plate 128.

The operation of the needle driver of the third embodiment will be described below.

If the operator presses the pressing plate 128 against the impelling force of the impelling spring 130, the distal end surface of the drive pin 132 fixedly attached to the pressing plate 128 and the distal end surface of the curved section 129 are engaged, and the curved section 129 is guided by the guide groove 137 and slides to the base side of the operation unit 2B.

That is, the transmission rod 28 is pulled toward the base side of the operation unit 2B via the pressing operation of the pressing plate 128, and the distal end of the curved section 48, which is the end section of the transmission rod 28, moves toward the proximal end section side of the plate spring 44 against the impelling force of the plate spring 44. As a result, the free end section of the plate spring 44 is pressed and moved in the direction of going away from the sandwiching plate 32a.

On the other hand, when no external force is applied to the pressing plate 128, the transmission rod 28 is held in a position closer to the treatment unit 4 side by the impelling force of the impelling spring 130. That is, the distal end of the curved section 48 is also held in a state of being positioned on the distal end side of the free end section of the spring by the impelling force of the plate spring 44. Furthermore, at this time, the plate spring 44 is held in a state where the distal end of the free end section thereof is pulled by this impelling force in the direction of approaching the sandwiching plate 32a.

Thus, similarly to the first embodiment, the transmission rod 28 moves in the long axis direction of the insertion unit 3, following the operation of pressing the pressing plate 128, and this movement causes a swinging movement of the free end section of the plate spring 44 via the movement of the curved section 48. Furthermore, following the swinging movement of the free end section of the plate spring 44, the second jaw 41 moves with respect to the first jaw 40 and the opening and closing action of the clamping surface 40*b* and clamping surface 42*b* is realized.

The turn action of the treatment unit 4 is identical to that of the first embodiment and the explanation thereof is herein omitted.

Thus, with the needle driver of the third embodiment, similarly to the first embodiment, the surgeon can perform the operations of opening and closing and turning the treatment unit that clamps and turns the curved needle for anastomosis by operations only with prescribed one finger. Thus, two operations, that is, the turn operation and opening and closing operation of the treatment unit can be conducted with a single finger, the operations are simple and the finger operating the operation dial 23 may act independently even in the course of operating the treatment unit 4. Therefore, the operation unit 2A can be clamped with good stability, positioning of the distal end of the curved needle 80 for anastomosis clamped by the treatment unit 4 is facilitated, the needle can be moved accurately, and anastomosis quality during surgery can be improved. Furthermore, because the operations are facilitated, the surgery time is shortened, burden on the patient is reduced, the stay period of the patient in the hospital is shortened, the patient can be rapidly returned to society, the turn-around efficiency of beds for hospitalized patients is increased, and effective hospital management can be realized.

Furthermore, with the third embodiment, though the input section for an opening and closing operation force (pressing plate 128) and the input section for a turn force (operation dial 23) are provided separately, those two input sections are provided very close to each other. The resultant effect is that the independent operations of opening and closing and turn can be performed exactly, that is, a risk of inadvertently performing an erroneous operation is low and the time required for the doctor to perform an operation is shortened.

Furthermore, because the opening and closing force input section (pressing plate 128) is located on the base side with respect to the operation dial 23 (toward the end back side with respect to the point where the instrument is supported) and the distal end is not shaken even during the pressing operation, the needle can be moved accurately and anastomosis quality during surgery can be improved.

Fourth Embodiment

The fourth embodiment of the present invention will be described below.

Figure 20:
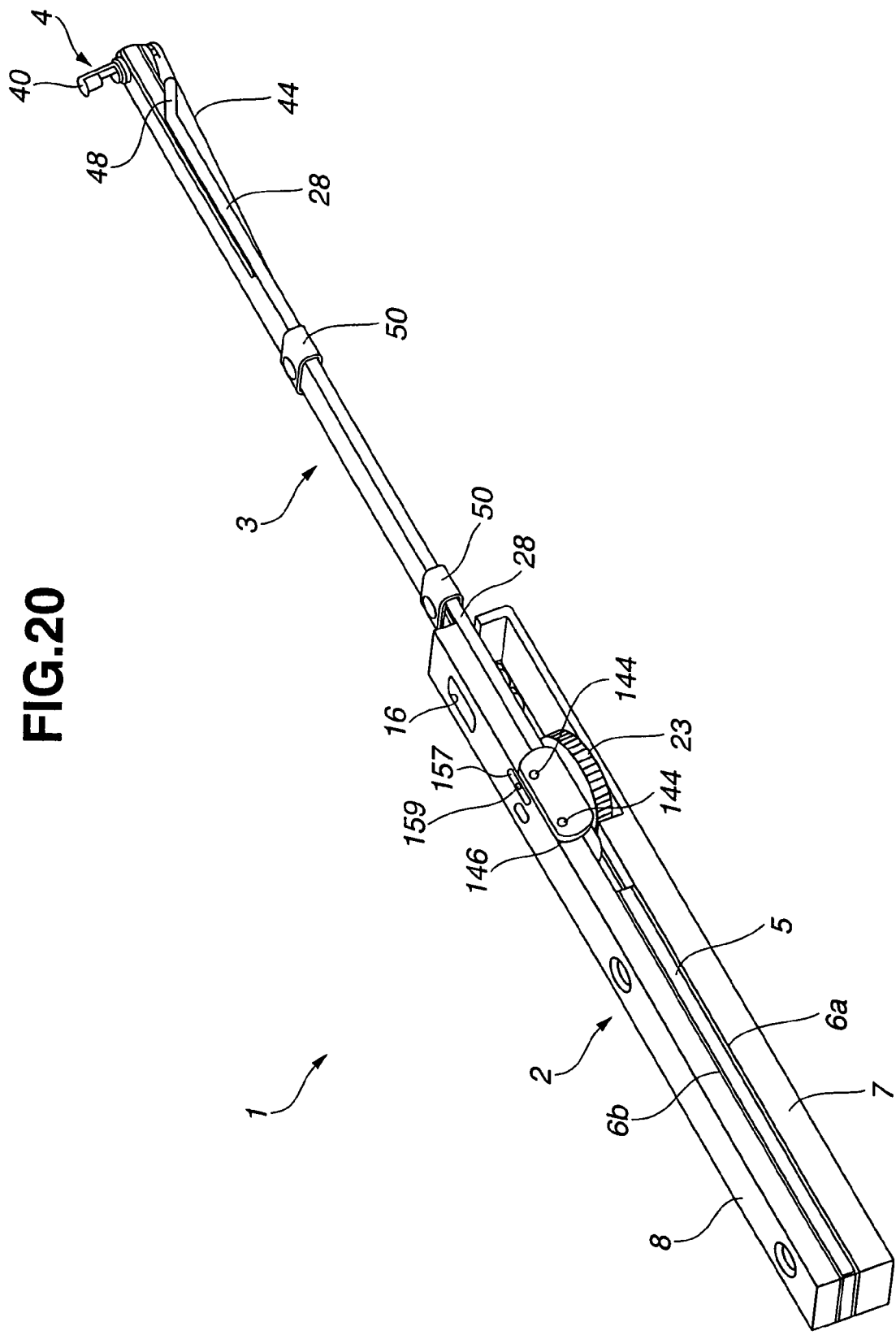
FIG. 20 is a perspective view illustrating the external appearance of the needle driver of a fourth embodiment of the present invention.
Figure 21:
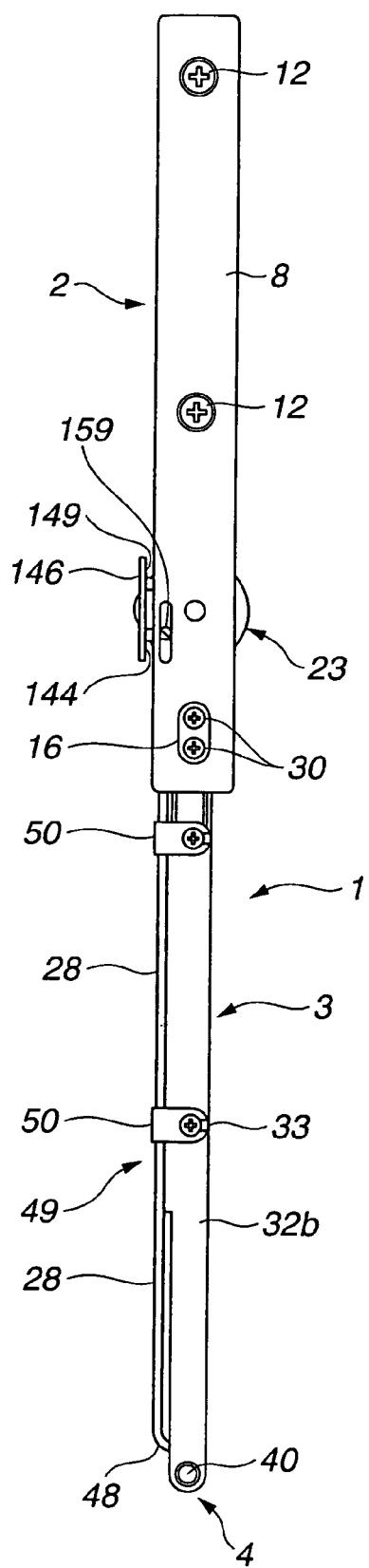
FIG. 21 is a front view of the needle driver of the fourth embodiment.
Figure 22:
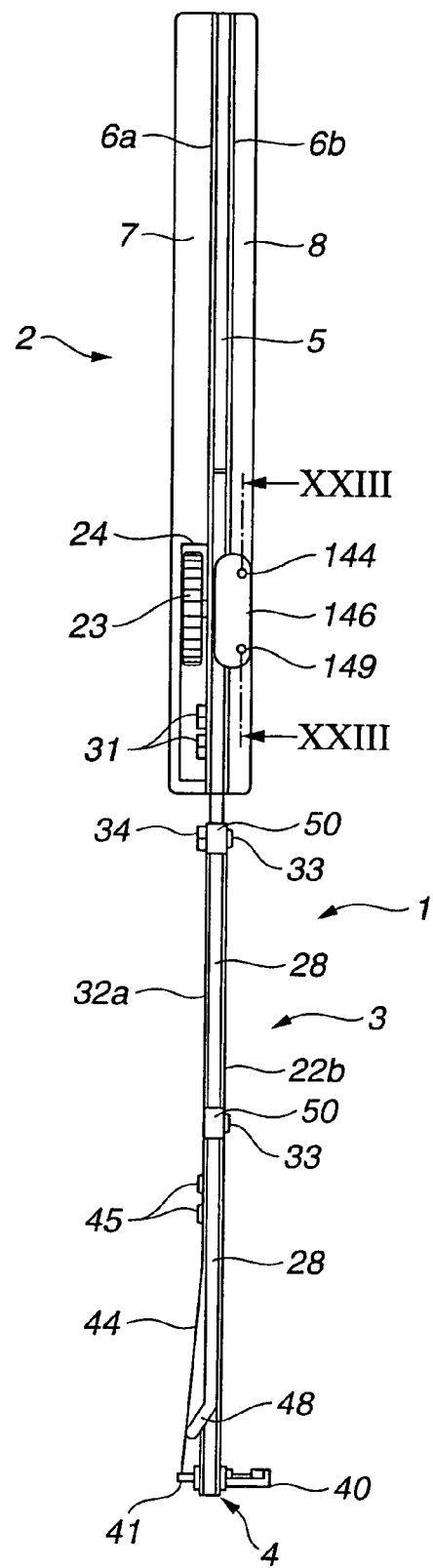
FIG. 22 is a side view of the needle driver of the fourth embodiment where one side surface thereof is shown.
Figure 23:
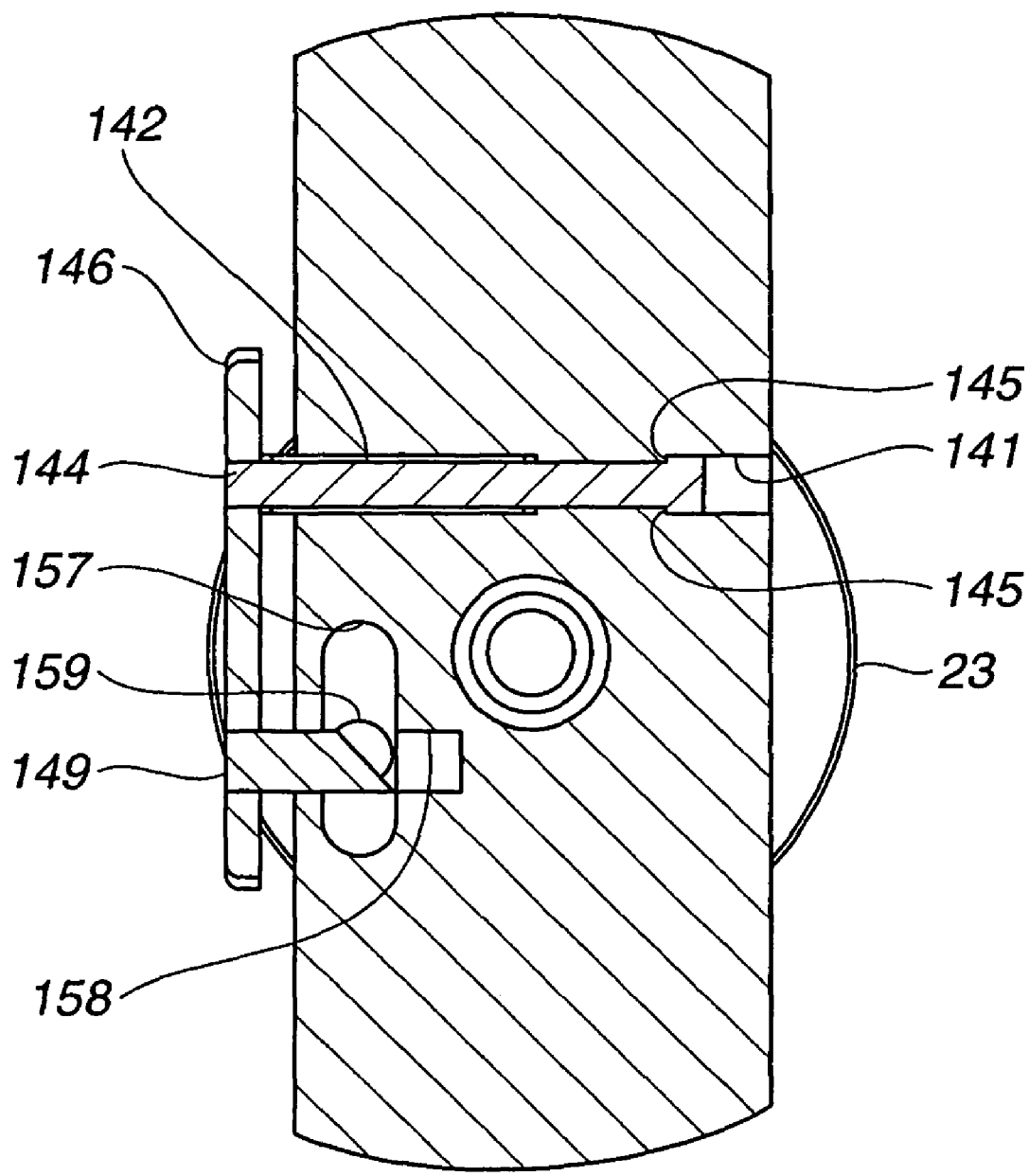
FIG. 23 is a sectional view where the needle driver of the fourth embodiment is shown as cut by the XXIII-XXIII section shown in FIG. 22.

FIG. 20 through FIG. 23 relate to the fourth embodiment of the present invention. FIG. 20 is a perspective view illustrating the external appearance of the needle driver of the fourth embodiment of the present invention. FIG. 21 is a front view of the needle driver of the fourth embodiment. FIG. 22 is a side view of the needle driver of the fourth embodiment where one side surface thereof is shown. FIG. 23 is a sectional view where the needle driver of the fourth embodiment is shown as cut by the XXIII-XXIII section shown in FIG. 22.

Because the basic structure of the needle driver of the fourth embodiment is identical to that of the first to third embodiments, in particular the third embodiment, only the difference therebetween will be explained and the explanation of identical components will be omitted.

As shown in FIG. 20 through FIG. 23, the needle driver 1C of the fourth embodiment differs from the needle driver of the third embodiment only by the configuration of the operation unit 2C, in particular by the configuration of the pressing plate for an opening and closing drive. The insertion unit 3 and treatment unit 4 are identical to those of the third embodiment.

The difference between the configuration of the operation unit 2C of the fourth embodiment and that of the operation unit 2B of the third embodiment described above will be explained hereinbelow with reference to FIG. 20 through FIG. 23.

Similarly to the operation unit 2, the operation unit 2C is provided with a first fixing plate 5, sandwiching plates 6*a*, 6*b*, first handle 7, and second handle 8.

Furthermore, a gap 17 is formed between the distal end surface of the first fixing plate 5 and the proximal end surface of the second fixing plate 13, an operation pulley 18 is provided in this gap 17, and an operation dial shaft 19 serving, too, as a shaft of the below-described operation dial 23 is passed through and fixed in the center of the operation pulley 18. A sliding bearing 20*a* abuts against the end section 19*a* of the operation dial shaft 19 on the side of the first handle 7, and a sliding bearing 20*b* abuts against the end section 19*b* on the side of the second handle 8. The operation dial shaft 19 is freely turnably supported by those sliding bearings 20*a*, 20*b*.

In the fourth embodiment, too, the diameter of the operation dial 23 is larger than the width (width in the short axis direction) of the first handle 7, a part of the outer peripheral surface of the operation dial protrudes outward to the both sides from the openings 24 in both end surfaces of the first handle 7, a sliding stopper is provided by roulette processing on the outer peripheral surface, and the operation dial 23 is turned by a finger of the operator of the needle driver 1B, thereby transmitting the turn force to the operation pulley 18 via the operation dial shaft 19. Furthermore, the belt 25 is stretched over the operation pulley 18.

A mechanism for transmitting the force providing for opening and closing operation of the treatment unit 4 in the fourth embodiment will be explained below.

As shown in FIG. 20 through FIG. 23, a pressing plate 146 for opening and closing drive of the treatment unit 4 is provided on one side of the operation unit 2C in the vicinity of the operation dial 23.

Furthermore, a guide groove 157 extending in the long axis direction of the operation unit 2C is formed in the vicinity of the pressing plate 146 in the surface of the second handle 8.

On the other hand, a transmission rod 28 (similar to that of the first embodiment) for linking the force associated with the operation of the pressing plate 146 in the operation unit 2C with the opening and closing operation of the first jaw 40 and second jaw 41 (see the first embodiment) in the treatment unit 4 is provided along the other side of the insertion unit 3. In the transmission rod 28, an L-shaped curved section 159 is formed at the end thereof on the side of the operation unit 2C, and the distal end of the curved section 159 is freely slidably engaged with the guide groove 157.

In the fourth embodiment, a slanted surface 155 tilted against the long axis direction of the operation unit 2C is formed, as shown in FIG. 23, in the distal end of the curved section 159.

The engagement relationship of the pressing plate 146 and curved section 159 will be described below.

As shown in FIG. 23, a through hole 141 is provided in one side of the operation dial 23 on the second handle 8, and small-diameter locking sections 145 are formed respectively at both sides of the through hole 141. An engagement pin 144 is slidably inserted into the through hole 141, one end of the engagement pin 144 is formed to have a large diameter, and the movement thereof is controlled by the locking section 145. The other end of the engagement pin 144 is mated with and fixed in a through hole formed in the pressing plate 146. Furthermore, an impelling spring 142 is wound around the engagement pin 144. The pressing plate 146 is impelled thereby in the direction of going away from the second handle 8.

On the other hand, the slanted surface 155 is formed, as described above, at the distal end of the curved section 159 and slidably inserted into the guide groove 157. An orifice 158 is provided in the same direction as the through hole 141 in the guide groove 157. In the orifice 158, a drive pin 149 having formed thereon a slanted surface cut at substantially the same angle as the slanted surface 155 is inserted in the position facing the slanted surface 155 of the curved section 159. Furthermore, the other end of the drive pin 149 is mated with and fixed in the through hole formed in the pressing plate 146.

The operation of the needle driver of the fourth embodiment will be described below.

If the operator presses the pressing plate 146 against the impelling force of the impelling spring 142, the distal end surface of the drive pin 149 fixedly attached to the pressing plate 146 and the distal end slanted surface 155 of the curved section 159 are engaged, and the curved section 159 is guided by the guide groove 157 and slides to the base side of the operation unit 2C.

That is, the transmission rod 28 is pulled toward the base side of the operation unit 2C by the pressing operation of the pressing plate 146, and the distal end of the curved section 48, which is the end section of the transmission rod 28, moves toward the proximal end section side of the plate spring 44 against the impelling force of the plate spring 44. As a result, the free end section of the plate spring 44 is pressed and moved in the direction of going away from the sandwiching plate 32a.

On the other hand, when no external force is applied to the pressing plate 146, the transmission rod 28 is held in a position closer to the treatment unit 4 side by the impelling force of the impelling spring 142. Thus, the distal end of the curved section 48 is also held in a state of being positioned on the distal end side of the free end section of the spring by the impelling force of the plate spring 44. Furthermore, at this time, the plate spring 44 is held in a state where the distal end of the free end section thereof is pulled by this impelling force in the direction of approaching the sandwiching plate 32a.

Thus, similarly to the first embodiment, the transmission rod 28 moves in the long axis direction of the insertion unit 3, following the operation of pressing the pressing plate 146, and this movement causes a swinging movement of the free end section of the plate spring 44 via the movement of the curved section 48. Furthermore, following the swinging movement of the free end section of the plate spring 44, the second jaw 41 moves with respect to the first jaw 40 and the opening and closing action of the clamping surface 40b and clamping surface 42b is realized.

The turn action of the treatment unit 4 is identical to that of the first embodiment and the explanation thereof is herein omitted.

Thus, with the needle driver of the fourth embodiment, similarly to the first embodiment, the surgeon can perform the operations of opening and closing and turning the treatment unit that clamps and turns the curved needle for anastomosis by operations only with prescribed one finger. Thus, two operations, that is, the turn operation and opening and closing operation of the treatment unit can be conducted with a single finger, the operations are simple and the finger operating the operation dial 23 may act independently even in the course of operating the treatment unit 4. Therefore, the operation unit 2A can be clamped with good stability, positioning of the distal end of the curved needle 80 for anastomosis clamped by the treatment unit 4 is facilitated, the needle can be moved accurately, and anastomosis quality during surgery can be improved. Furthermore, because the operations are facilitated, the surgery time is shortened, burden on the patient is reduced, the stay period of the patient in the hospital is shortened, the patient can be rapidly returned to society, the turnaround efficiency of beds for hospitalized patients is increased, and effective hospital management can be realized.

Furthermore, with the fourth embodiment, similarly to the third embodiment, though the input section for an opening and closing operation force (pressing plate 146) and the input section for a turn force (operation dial 23) are provided separately, those two input sections are provided very close to each other. The resultant effect is that the independent operations of opening and closing and turn can be performed exactly, that is, a risk of inadvertently performing an erroneous operation is low and the time required for the doctor to perform an operation is shortened.

A modification example of the treatment unit 4 will be described below.

Figure 24:
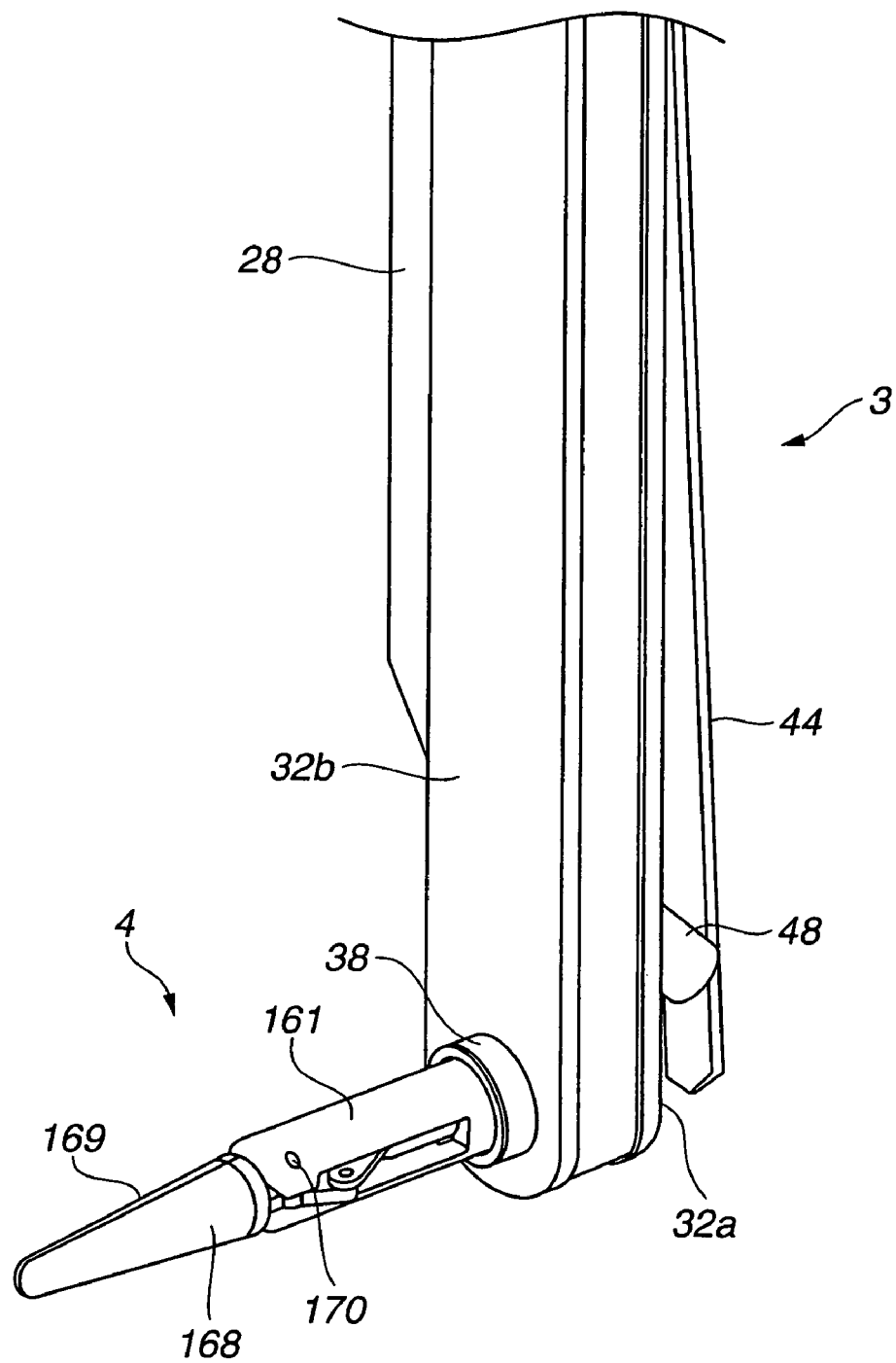
FIG. 24 is a main-part enlarged perspective view illustrating a modification example of the treatment unit in the first to fourth embodiments of the present invention.
Figure 25:
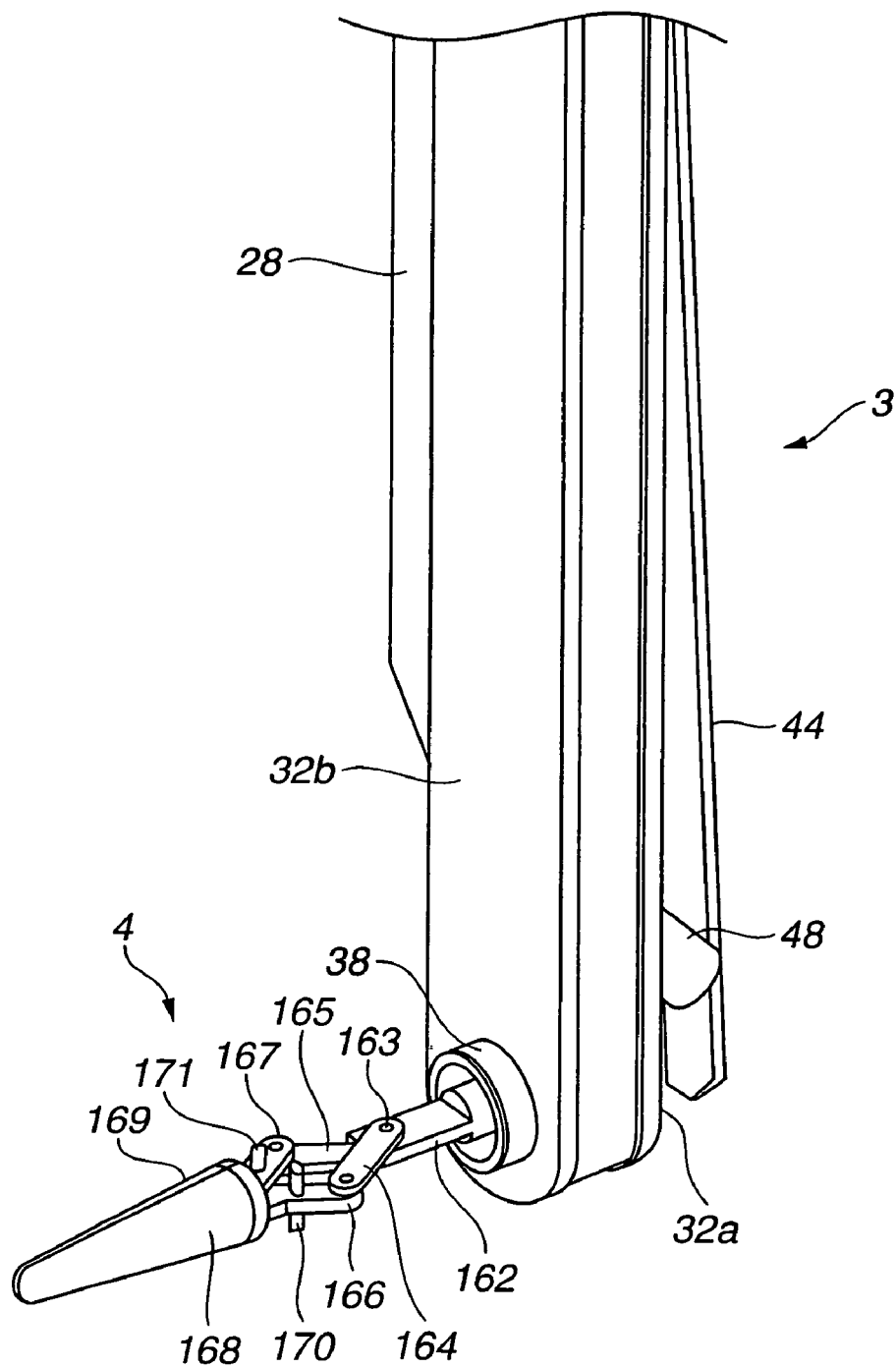
FIG. 25 is a main-part enlarged perspective view illustrating a modification example of the treatment unit in the first to fourth embodiments of the present invention.

FIG. 24 is a main-part enlarged perspective view illustrating the modification example of the treatment unit in the needle driver of the first to fourth embodiments of the present invention. FIG. 25 is a main-part enlarged perspective view illustrating the modification example of the treatment unit in greater detail.

In the needle driver of each above-described embodiment, the treatment unit 4 can also have a grasping forceps structure in which an object to be clamped is grasped with two facing clamping pieces shown in FIG. 24 and FIG. 25.

As shown in FIG. 24 and FIG. 25, an outer tube 161 protruding sidewise at a right angle with respect to the insertion unit 3 is provided integrally on a turn pulley 37 (sliding bearing 38) provided in the treatment unit 4A. A through hole is provided in the center of the turn pulley 37, and a transmission shaft 162 that can move back and forth in the axial direction is provided in this through hole.

The proximal end section of the transmission shaft 162 is turnably installed in the notch 46, a pin 163 is passed through and fixed to the distal end section of the transmissions shaft 162, and a link 164 and a link 165 are freely turnably attached to the pin 163.

A pin 166 and a pin 167 are passed through and fixed to the distal end side of the link 164 and link 165, respectively, a clamping piece 168 is freely turnably attached to the pin 166, and the clamping piece 169 is freely turnably attached to the pin 167.

Pins 170, 171 are freely turnably passed through the middle sections of the clamping piece 168 and clamping piece 169, respectively, and those pins 170 and 171 are fixed to the outer tube 161. Furthermore, clamping surfaces 168a and 169a that face each other are formed at the clamping pieces 168, 169, respectively.

The operation of this modification example will be described below.

As described in each of the above-described embodiments, when the transmission rod 28 is pulled to the operation unit 2, the plate spring 44 is pressed and moved in the direction of going away from the sandwiching plate 32a and the transmission shaft 162 is retracted in the axial direction via the notch section 46. When the transmission shaft 162 is retracted, the links 164, 165 are pulled via the pin 163. At this time, the distal end sides of the clamping pieces 168, 169 are pulled via the pins 166, 167, respectively, and turn about the pins 170, 171. This clamping surfaces 168a, 169a are at this time opened.

When the transmission shaft 162 further advances forward, the links 164, 165 are pressed via the pin 163. At this time, the distal end sides of the clamping pieces 168, 169 are pressed via the pins 166, 167, respectively and turn about the pins 170, 171. The clamping surfaces 168a and 169a are at this time closed.

Furthermore, when the turn pulley 37 turns via the operation pulley 18 and belt 25 by the turn of the operation dial 23, the outer tube 161 turns integrally therewith, and the clamping pieces 168 and 169 turn via the pins 170 and 171.

With this modification example, since the treatment unit 4 has a grasping forceps structure, a universal clamping instrument is provided that can clamp objects other than the curved needle, too. Therefore, it is not necessary to replace the instrument according to the operation to be performed and the surgery time can be shortened.

As a result, burden on the patient can be reduced, the stay period of the patient in the hospital can be shortened, the patient can be rapidly returned to society, the turnaround efficiency of beds for hospitalized patients is increased, and effective hospital management can be realized.

Fifth Embodiment

The fifth embodiment of the present invention will be described below.

Figure 26:
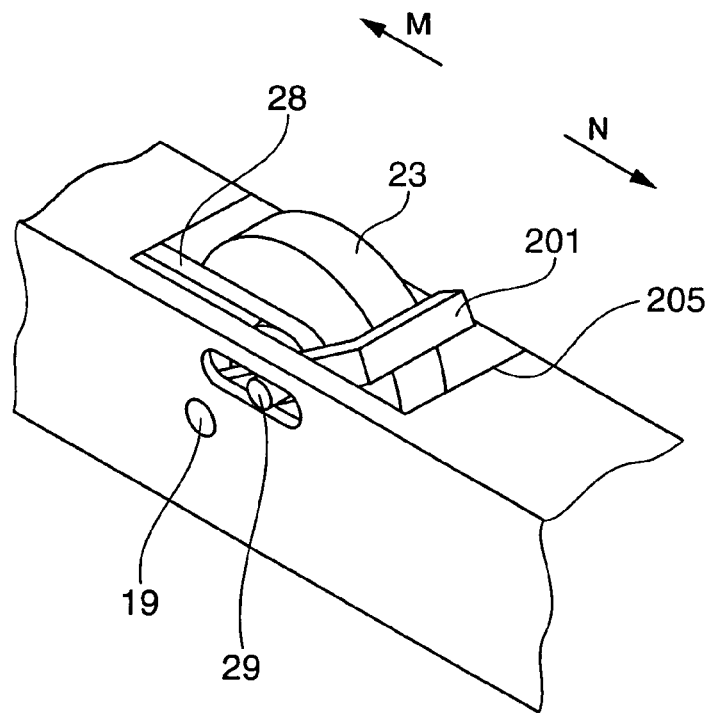
FIG. 26 is a main-part external enlarged perspective view illustrating the operation dial and peripheral components thereof in the needle driver of a fifth embodiment of the present invention.
Figure 27:
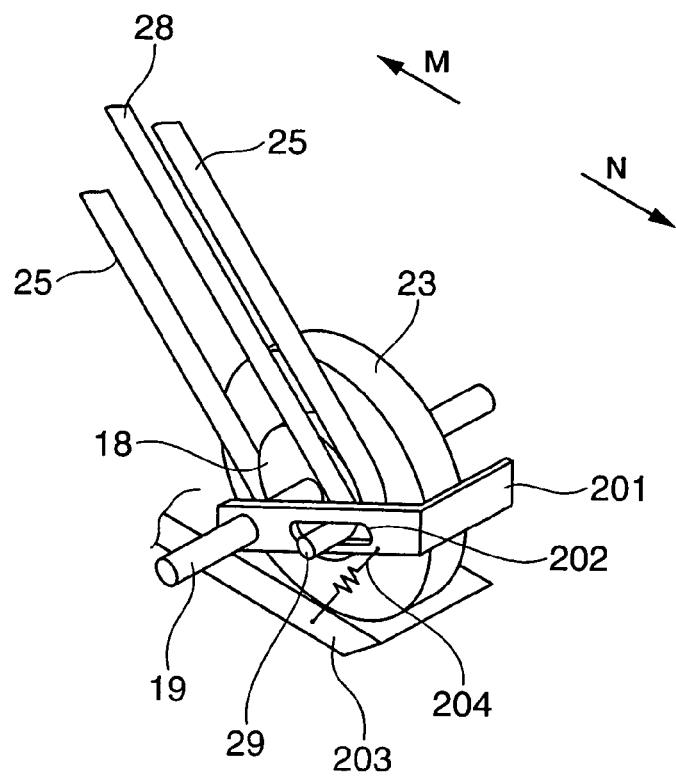
FIG. 27 is a main-part enlarged perspective view illustrating the operation dial and peripheral components thereof in the needle driver of the fifth embodiment of the present invention.

FIG. 26 and FIG. 27 relate to the fifth embodiment of the present invention. FIG. 26 is a main-part external enlarged perspective view illustrating the operation dial and peripheral components thereof in the needle driver of the fifth embodiment of the present invention. FIG. 27 is a main-part enlarged perspective view illustrating the operation dial and peripheral components thereof in the needle driver of the fifth embodiment of the present invention.

In the figures, the distal end side of the operation unit 2 is shown by arrow M and the end back side (base side) is indicated with arrow N.

Because the basic structure of the needle driver of the fifth embodiment is identical to that of the first embodiment, only the difference therebetween will be explained and the explanation of identical components will be omitted.

As shown in FIG. 26 and FIG. 27, the needle driver of the fifth embodiment differs from the needle driver of the first embodiment only by the configuration of the operation unit 2. The insertion unit 3 and treatment unit 4 are identical to those of the first embodiment. The difference between the configuration of the operation unit 2 of the fifth embodiment and that of the operation unit 2 of the first embodiment described above will be explained hereinbelow with reference to FIG. 26 and FIG. 27.

As shown in FIG. 26, an operation dial shaft 19 passes freely turnably through one end of an opening and closing lever 201 having an L-like shape. A long hole 202 is formed in the middle section of the opening and closing lever 201, and the curved section 29 of the transmission rod 28 is inserted so that it can freely slide in the long-diameter direction. A spring 204 is disposed in a compressed state between the opening and closing lever 201 and the inner surface 203 of the handle. As a result, the other end of the opening and closing lever 201 is impelled in the direction of exposure from a handle opening 205.

In the needle driver of the fifth embodiment, when the exposed portion of the opening and closing lever 201 that is exposed from the opening 205 is pulled toward the end back side (base side) of the operation unit 2, the opening and closing lever 201 turns about the operation dial shaft 19. As a result, the curved section 29 is pulled toward the end back side of the operation unit 2, while sliding in the direction of going away from the operation dial shaft 19 inside the long hole 202.

Following this movement, the transmission rod 28 is also pulled toward the end back side, and the distal end of the curved section 48, which is the end section thereof, moves toward the proximal end section of the plate spring 44 against the impelling force of the plate spring 44. As a result, the free end section of the plate spring 44 is pressed and moved in the direction of going away from the sandwiching plate 32a.

On the other hand, when no external force is applied to the opening and closing lever 201, the transmission rod 28 is held in a position closer to the treatment unit 4 by the impelling force of the impelling spring 204. That is, the distal end of the curved section 48 is also held in a state where it is positioned on the distal end side of the free end section of the spring by the impelling force of the plate spring 44. Furthermore, at this time, the plate spring 44 is held in a state where the distal end of the free end section thereof is pulled in the direction of approaching the sandwiching plate 32a by the impelling force of the spring.

Thus, similarly to the first embodiment, the transmission rod 28 moves in the long axis direction of the insertion unit 3, following the operation of turning the opening and closing lever 201, and this movement causes a swinging movement of the free end section of the plate spring 44 via the movement of the curved section 48. Furthermore, following the swinging movement of the free end section of the plate spring 44, the second jaw 41 moves with respect to the first jaw 40 and the opening and closing action of the clamping surface 40b and clamping surface 42b is realized.

The turn action of the treatment unit 4 is identical to that of the first embodiment and the explanation thereof is herein omitted.

Thus, with the needle driver of the fifth embodiment, similarly to the first embodiment, the surgeon can perform the operations of opening and closing and turning the treatment unit that clamps and turns the curved needle for anastomosis by operations only with prescribed one finger. Thus, two operations, that is, the turn operation and opening and closing operation of the treatment unit can be conducted with a single finger.

Furthermore, both the operation dial 23 and the opening and closing lever 201 are operated in the direction of moving back and forth toward the direction of the long axis of the operation unit so that the operations are simple. Therefore, the fatigue of the doctor using the device is reduced and quality of surgery is improved. As a result, the recovery of the patient is accelerated, the stay period of the patient in the hospital is shortened, the patient can be rapidly returned to society, the turnaround efficiency of beds for hospitalized patients is increased, and effective hospital management can thus be realized.

Sixth Embodiment

The sixth embodiment of the present invention will be described below.

Figure 28:
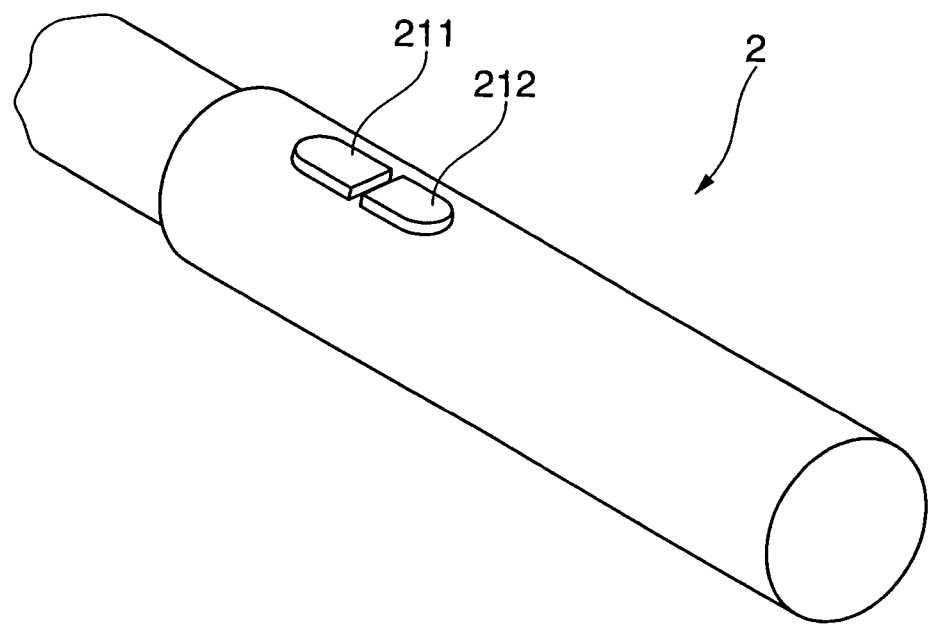
FIG. 28 is a main-part external enlarged perspective view illustrating the operation switch in the needle driver of a sixth embodiment of the present invention.
Figure 29:
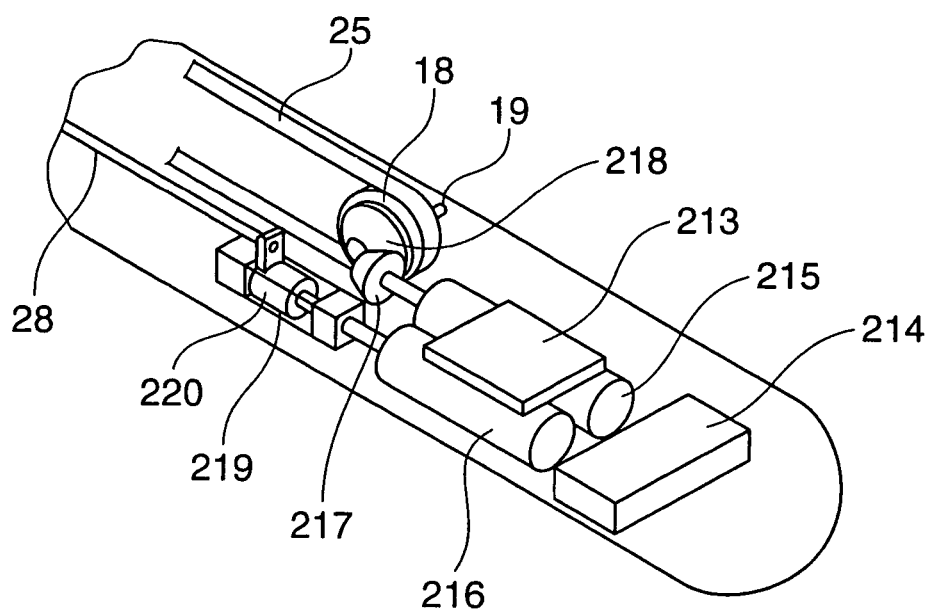
FIG. 29 is a main-part enlarged perspective view illustrating the opening and closing force generation mechanism and a turn force generation mechanism in the needle driver of the sixth embodiment.

FIG. 28 and FIG. 29 relate to the sixth embodiment of the present invention. FIG. 28 is a main-part external enlarged perspective view illustrating the operation switch in the needle driver of the sixth embodiment of the present invention. FIG. 29 is a main-part enlarged perspective view illustrating the opening and closing force generation mechanism and a turn force generation mechanism in the needle driver of the sixth embodiment of the present invention.

Because the basic structure of the needle driver of the sixth embodiment is identical to that of the first embodiment, only the difference therebetween will be explained and the explanation of identical components will be omitted.

As shown in FIG. 28 and FIG. 29, the needle driver of the sixth embodiment differs from the needle driver of the first embodiment only by the configuration of the operation unit 2. The insertion unit 3 and treatment unit 4 are identical to those of the first embodiment. The difference between the configuration of the operation unit 2 of the sixth embodiment and that of the operation unit 2 of the first embodiment described above will be explained hereinbelow with reference to FIG. 28 and FIG. 29.

As shown in FIG. 26, in the needle driver of the sixth embodiment, a first operation switch 211 and a second operation switch 212 are disposed in a row in the long axis direction in the operation unit 2. The first operation switch 211 and second operation switch 212 are connected to a control panel 213, and the control panel 213 is connected to a power source 214 disposed inside the operation unit 2 for power supply.

A turn motor 215 that is a turn force generation source and an opening and closing motor 216 that is an opening and closing force generation source are connected to the control panel 213 and equipped with control circuits thereof (not shown in the figures).

A beveled gear 217 is fixed to the output shaft of the turn motor 215, and the beveled gear 217 is engaged at a right angle with a beveled gear 218 fixed to the operation dial shaft 19 matching the central axes thereof.

On the other hand, a so-called ball screw 219 that converts a turn movement into a linear movement is connected to the output shaft of the opening and closing motor 216, and the end back of the transmission rod 28 is fixed to a slider 220 of the ball screw 219.

In the needle driver of the sixth embodiment, both the turn motor 215 and the opening and closing motor 216 are in a stationary state when both the first operation switch 211 and second controls witch 212 are not pressed.

When only the first operation switch 211 is pressed in this stationary state, the turn motor 215 will be controlled by the control panel 213 so as to turn at the prescribed rate in the counterclockwise direction, as viewed from the end back side of the operation unit 2. As a result, the operation pulley 18 will turn in one direction via the beveled gears 217, 218 and the treatment unit 4 will turn in one direction via the belt 25 and turn pulley 37.

On the other hand, when only the second operation switch 212 is pressed in the stationary state, the turn motor 215 will be controlled by the control panel 213 so as to turn at the prescribed rate in the clockwise direction, as viewed from the end back side of the operation unit 2. As a result, the operation pulley 18 will turn in the other direction via the beveled gears 217, 218 and the treatment unit 4 will turn in the other direction via the belt 25 and turn pulley 37.

Furthermore, when the first operation switch 211 and the second operation switch 212 are pressed simultaneously, the opening and closing motor 216 will be controlled by the control panel 213 so as to turn at the prescribed rate in the clockwise direction, as viewed from the end back side of the operation unit 2. As a result, the slider 220 of the ball screw 219 moves toward the end back side, the transmission rod 28 connected thereto is pulled to the end back side, and the distal end of the curved section 48, which is the end section of the transmission rod, moves to the proximal end side of the plate spring 44 against the impelling force of the plate spring 44. As a result, the free end section of the plate spring 44 is pressed and moved in the direction of going away from the sandwiching plate 32a and the treatment unit 4 opens. Thus, the second jaw 41 moves with respect to the first jaw 40 and the clamping surface 40b and clamping surface 42b open.

Furthermore, when the state in which the first operation switch 211 and the second operation switch 212 are pressed simultaneously is released, the opening and closing motor 216 is controlled by the control panel 213 so as to turn at the prescribed speed in the counterclockwise direction, as viewed from the end back side of the operation unit 2, that is in the reverse direction. The turn control of opening and closing motor 216 is continued till the treatment unit 4 is closed.

On the other hand, when neither the first operation switch 211 nor the second operation switch 212 is pressed, the slider 220 of the ball screw 219 remains in a stationary state, the transmission rod 28 is held in a position closer to the treatment unit 4, and the distal end of the curved section 48 is also held in a state where it is positioned on the distal end side of the free end section of the plate spring by the impelling force of the plate spring 44. Furthermore, at this time, the plate spring 44 is held in a state where the distal end of the free end section thereof is pulled in the direction of approaching the sandwiching plate 32a by the impelling force of the spring.

Thus, in response to the switch operation of the first operation switch 211 and second operation switch 212, similarly to the first embodiment, the transmission rod 28 moves in the long axis direction of the insertion unit 3, thereby causing a swinging movement of the free end section of the plate spring 44 via the movement of the curved section 48. Furthermore, in response to the swinging movement of the free end section of the plate spring 44, the second jaw 41 moves with respect to the first jaw 40, and opening and closing action of the clamping surface 40b and clamping surface 42b is executed.

With the needle driver of the sixth embodiment, because the turn force is generated by a motor drive, the surgeon has to apply a force only such as required to press the operation switch and the fatigue level is low.

Furthermore, the two operation switches have to be pressed simultaneously to open the treatment unit and foolproof structure is provided which prevents the treatment unit from being opened erroneously. As a result, the patient can undergo high-quality surgery, the stay period of the patient in the hospital is shortened, the patient can be rapidly returned to society, the turnaround efficiency of beds for hospitalized patients is increased, and effective hospital management can thus be realized.

Seventh Embodiment

The seventh embodiment of the present invention will be described below.

Figure 30:
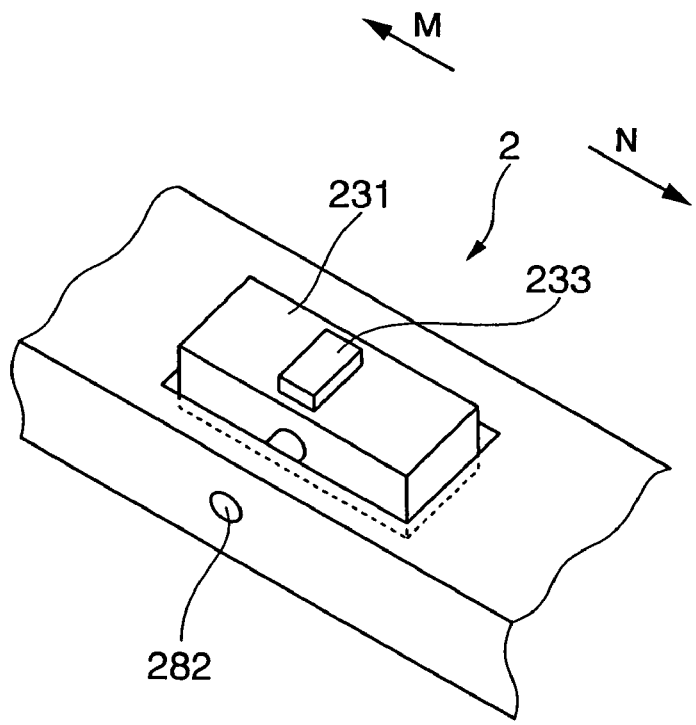
FIG. 30 is a main-part external enlarged perspective view illustrating the operation switch in the needle driver of a seventh embodiment of the present invention.
Figure 31:
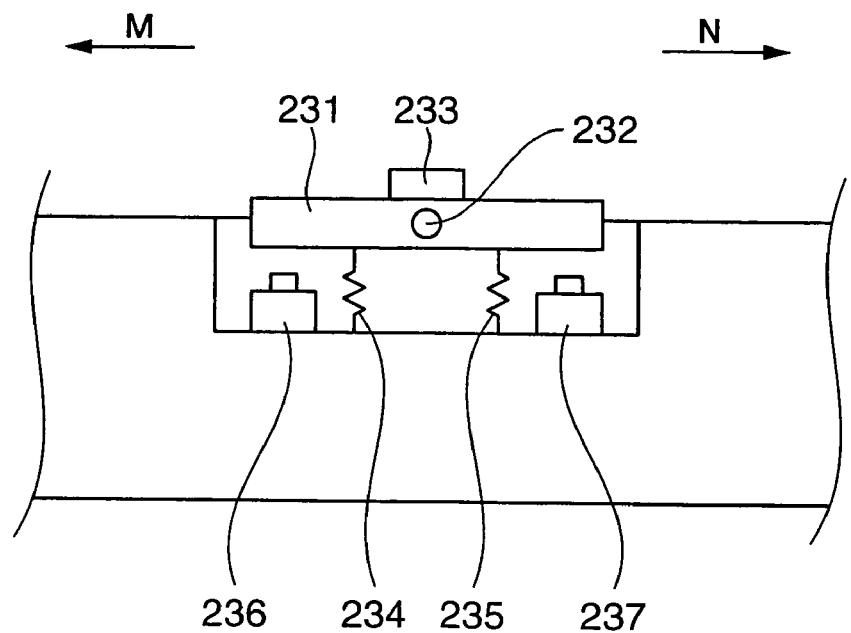
FIG. 31 is a main-part enlarged perspective view illustrating the opening and closing force generation switch and a turn force generation switch in the needle driver of the seventh embodiment.

FIG. 30 and FIG. 31 relate to the seventh embodiment of the present invention. FIG. 30 is a main-part external enlarged perspective view illustrating the operation switch in the needle driver of the seventh embodiment of the present invention. FIG. 31 is a main-part enlarged perspective view illustrating the opening and closing force generation switch and a turn force generation switch in the needle driver of the seventh embodiment.

Because the basic structure of the needle driver of the seventh embodiment is identical to that of the sixth embodiment, only the difference therebetween will be explained and the explanation of identical components will be omitted.

That is, the needle driver of the seventh embodiment differs from the needle driver of the sixth embodiment only in the portion of operation switches, wherein motors are the generation sources of the opening and closing force and turn force in the sixth embodiment. Other features are identical to those of the sixth embodiment. For example, the opening and closing force generation mechanism and turn force generation mechanism have a structure identical to those of the needle driver of the sixth embodiment, which is shown in FIG. 29.

As shown in FIG. 30 and FIG. 31, the needle driver of the seventh embodiment comprises a turn operation switch 231 and a switch 233 for opening and closing control in the operation unit 2.

The turn operation switch 231 is freely turnably supported by a turn shaft 232, and both ends of the turn shaft 232 are fixed to the operation unit 2. The switch 233 for opening and closing control is attached to the central section of the upper surface of the turn operation switch 231.

Both the turn operation switch 231 and the switch 233 for opening and closing control are connected to the control panel 213 (see FIG. 29).

Furthermore, two compression springs 234, 235 with identical characteristics are provided in symmetrical positions with respect to the turn shaft 232 on the undersurface of the turn operation switch 231, and the turn operation switch 231 is held so as to remain in a position parallel to the long axis direction of the operation unit 2.

A contact switch 236 is fixed to the operation unit 2 in the lower direction of the distal end side of the turn operation switch 231, and a contact switch 237 is fixed to the operation unit in the lower direction of the end back side of the turn operation switch 231.

In the needle driver of the seventh embodiment, when the distal end side of the turn operation switch 231 is pressed, the turn operation switch 231 swings about the turn shaft 232. As a result, the lower surface of the distal end side of the turn operation switch 231 presses the switch 236. Following this action, the control panel 213 drives the turn motor 215 so that the treatment unit 4 turns in the same direction as the swinging direction of the turn operation switch 231.

On the other hand, when the switch 233 for opening and closing control is pressed, the control panel 213 unidirectionally turns and drives the opening and closing motor 216 in the direction of opening the treatment unit 4. When the pressing action of the switch 233 for opening and closing control is released in a state where the treatment unit 4 is open, the control panel 213 turns and drives the opening and closing motor 216 in the other direction till the treatment unit 4 is closed.

Furthermore, when the end back side of the turn operation switch 231 is pressed, the turn operation switch 231 swings about the turn shaft 232. As a result, the lower surface of the end back side of the turn operation switch 231 presses the switch 237. Following this action, the control panel 213 drives the turn motor 215 so that the treatment unit 4 turns in the same direction as the swinging direction of the turn operation switch 231.

With the needle driver of the seventh embodiment, the turn operation unit and opening and closing operation unit are separated. Therefore, a risk of inadvertently performing an operation in the course of performing another operation is eliminated and the time required for the doctor to perform an operation is shortened. As a result, a larger number of patients can receive the benefit of surgery.

Eighth Embodiment

The eighth embodiment of the present invention will be described below.

Figure 32:
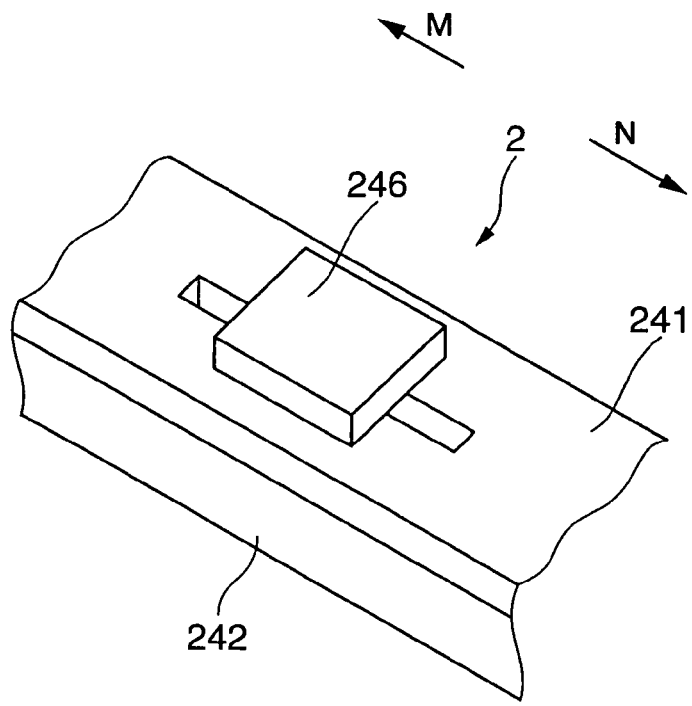
FIG. 32 is a main-part external enlarged perspective view illustrating the operation switch in the needle driver of an eighth embodiment of the present invention.
Figure 33:
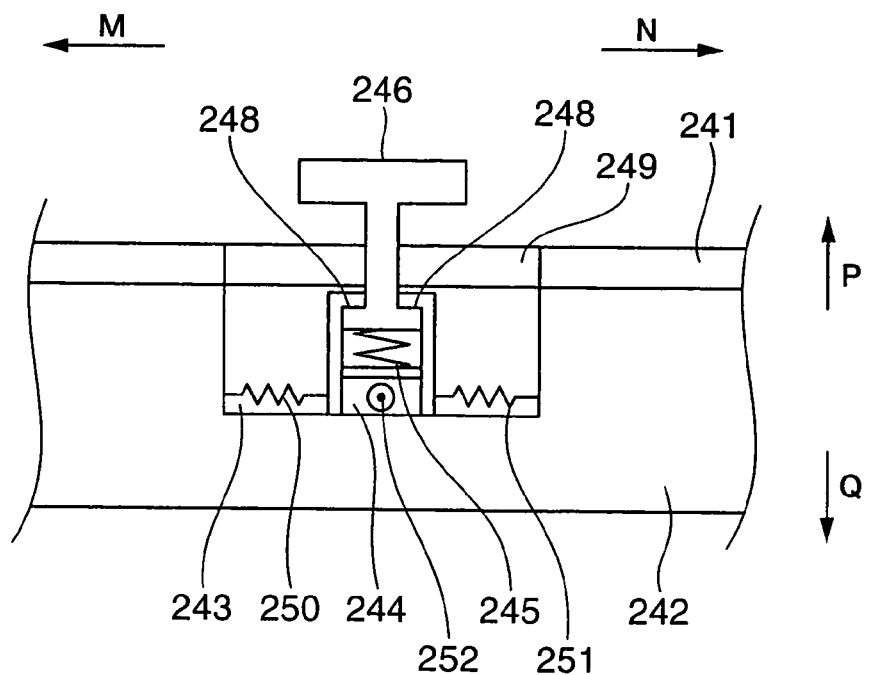
FIG. 33 is a main-part enlarged perspective view illustrating the opening and closing force generation switch and a turn force generation switch in the needle driver of the eighth embodiment.

FIG. 32 and FIG. 33 relate to the eighth embodiment of the present invention. FIG. 32 is a main-part external enlarged perspective view illustrating the operation switch in the needle driver of the eighth embodiment of the present invention. FIG. 33 is a main-part enlarged perspective view illustrating the opening and closing force generation switch and a turn force generation switch in the needle driver of the eighth embodiment.

Because the basic structure of the needle driver of the eighth embodiment is identical to that of the sixth embodiment, only the difference therebetween will be explained and the explanation of identical components will be omitted.

Thus, the needle driver of the eighth embodiment differs from the needle driver of the sixth embodiment only in the portion of operation switches, wherein motors are the generation sources of the opening and closing force and turn force in the sixth embodiment. Other features are identical to those of the sixth embodiment. For example, the opening and closing force generation mechanism and turn force generation mechanism have a structure identical to those of the needle driver of the sixth embodiment, which is shown in FIG. 29.

As shown in FIG. 32 and FIG. 33, the needle driver of the eighth embodiment comprises an upper lid 241 and a lower lid 242 in the operation unit 2, those lids being adhesively fixed to each other or tightened together with a screw. A turn operation slider 244 is disposed so that it can slide in the along axis direction, in a groove 243 provided in the lower lid 242. A contact switch 245 is fixed to the lower surface on the inner side of the turn operation slider 244, and the contact switch 245 is connected to the control panel 213 (see FIG. 29).

Furthermore, a turn roller 252 is attached to the lower surface on the outer side of the turn operation slider 244 and is brought into contact with the undersurface of the groove 243. An encoder (not shown in the figures) is provided on the same axis as the turn roller 252, and this encoder is connected to the control panel 213.

Furthermore, in the operation unit 2 of the eighth embodiment, an opening and closing operation button 246 is provided so that the lower end thereof can slide in the up-down direction inside the turn operation slider 244. The upper end of the opening and closing operation button 246 is provided so as to be exposed from a long hole 249 provided in the upper portion of the groove 243 and above the upper lid 241 as well.

A compressed spring 247 is provided between the upper surface of the contact switch 245 and the undersurface of the opening and closing operation button 246, and the opening and closing operation button 246 is impelled toward a step 248 provided above the turn operation slider 244.

Furthermore, a spring 250 is disposed between the distal end side of the turn operation slider 244 and the distal end side of the groove 243, and a spring 251 is provided between the end back side of the turn operation slider 244 and the end back side of the groove 243. The slider 244 is held to stay in the center of the groove 243.

In the needle driver of the eighth embodiment, when the opening and closing operation button 246 is pressed to the distal end side, the turn operation slider 244 moves toward the distal end side. Furthermore, in response to the movement of the turn operation slider 244, the turn roller 252 moves in one direction on the undersurface of the groove 243.

At this time, the control panel 213 calculates the distance traveled by the moving turn operation slider 244 from the central zone of the groove 243 to the distal end side using the value of the aforementioned encoder and drives the turn motor 215 (see FIG. 29) based on the calculation results so that the treatment unit 4 turns in one direction at a speed proportional to this distance.

On the other hand, when the opening and closing operation button 246 is pressed at the end back side, the turn operation slider 244 moves toward the end back side and in response to the movement of the turn operation slider 244 and the turn roller 252 moves in the other direction on the undersurface of the groove 243.

At this time, the control panel 213 calculates the distance traveled by moving turn operation slider 244 from the central zone of the groove 243 to the end back side using the value of the aforementioned encoder and drives the turn motor 215 (see FIG. 29) based on the calculation results so that the treatment unit 4 turns at a speed proportional to this distance in the reversed direction with respect to that in which the treatment unit 4 turned when the opening and closing operation button 246 is pressed to the distal end side.

Furthermore, when the opening and closing operation button 246 is pressed to the lower end side, the undersurface of the opening and closing operation button 246 presses against the contact switch 245, and in response to the ON operation of this switch 245, the control panel 213 drives the opening and closing motor 216 in the direction of opening. Furthermore, if the pressing operation of the opening and closing operation button 246 is released in the state where the treatment unit 4 is open, the control panel 213 drives the opening and closing motor 216 in the other direction till the treatment unit 4 is closed.

With the needle driver of the eighth embodiment, adjusting the position of the turn operation slider enables the fine control of the turn speed of the treatment unit. As a result, the patient can undergo high-quality surgery, the stay period of the patient in the hospital is shortened, the patient can be rapidly returned to society, the turnaround efficiency of beds for hospitalized patients is increased, and effective hospital management can thus be realized.

Ninth Embodiment

The ninth embodiment of the present invention will be described below.

Figure 34:
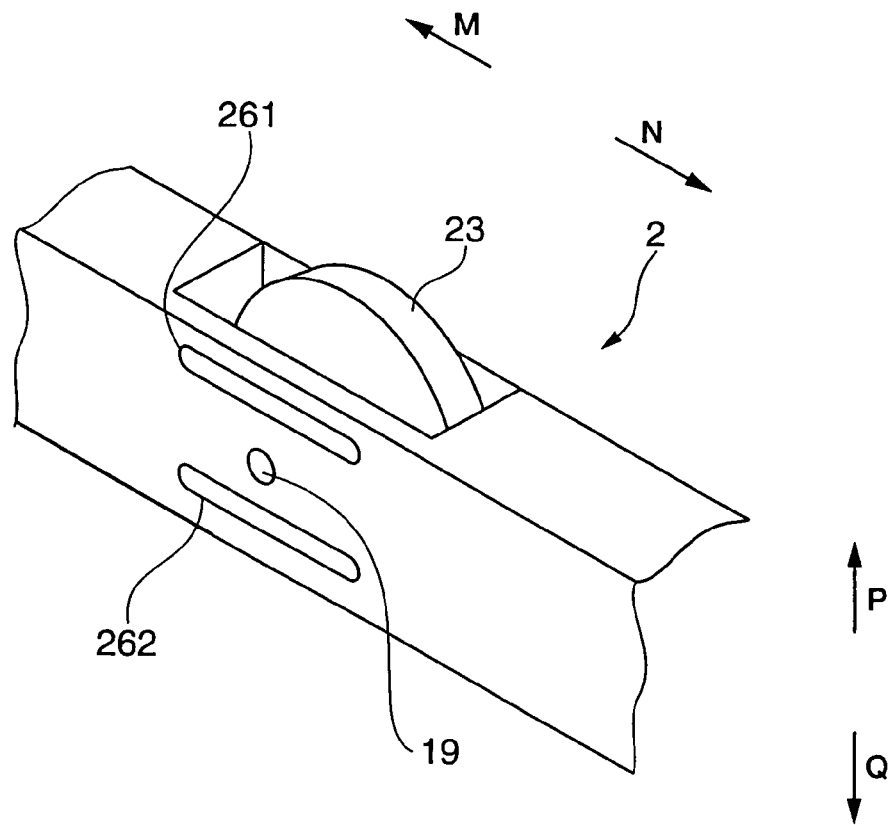
FIG. 34 is a main-part external enlarged perspective view illustrating the operation switch in the needle driver of a ninth embodiment of the present invention.

FIG. 34 is a main-part external enlarged perspective view illustrating the operation switch in the needle driver of the ninth embodiment of the present invention.

Because the basic structure of the needle driver of the ninth embodiment is identical to that of the first embodiment, only the difference therebetween will be explained and the explanation of identical components will be omitted.

That is, the needle driver of the ninth embodiment differs from the needle driver of the sixth embodiment only in the portion for operating the opening and closing force and turn force, wherein motors are the generation sources of the opening and closing force and turn force in the sixth embodiment. Other features are identical to those of the sixth embodiment. For example, the opening and closing force generation mechanism and turn force generation mechanism have a structure identical to those of the needle driver of the sixth embodiment, which is shown in FIG. 29.

As shown in FIG. 34, in the operation unit 2 of the ninth embodiment, the operation dial 23 is passed through and fixed together with the operation pulley 18 to the operation dial shaft 19, and both ends of the operation dial shaft 19 are freely turnably fixed to the operation unit 2.

Furthermore, in the operation unit 2, long holes 261, 262 extending in the long axis direction (arrows M and N in the figure) of the operation unit 2 are provided in both sides of the fixing portion of the operation dial shaft 19.

In the needle driver of the ninth embodiment, strain gages are pasted in the long holes 261, 262. The strain gages are connected to the control panel 213 (see FIG. 29) and detect the forces on both sides (shown by arrows P, Q in the figure; same hereinbelow) applied to the operation dial shaft 19. The strain gages and control panel 213 constitute a dial pressing force detection mechanism 263.

In the needle driver of the ninth embodiment, when the operation dial 23 is pressed sidewise, the pressing force thereof is detected via the operation dial shaft 19 by the dial pressing force detection mechanism 263. The control panel 213 drives the opening and closing motor 216 so that the treatment unit 4 opens by the length proportional to the detected pressing force.

On the other hand, when no external force is applied to the operation dial 23, the control panel 213 controls the opening and closing motor 216 so as to close the treatment unit 4.

The turn operation of the treatment unit 4 is identical to that of the first embodiment and, therefore, the explanation thereof is herein omitted.

With the needle driver of the ninth embodiment, the treatment unit is opened proportionally to the dial pressing force, thereby enabling a fine control of the opening degree of the treatment unit. As a result, the patient can undergo high-quality surgery, the stay period of the patient in the hospital is shortened, the patient can be rapidly returned to society, the turnaround efficiency of beds for hospitalized patients is increased, and effective hospital management can thus be realized.

Tenth Embodiment

The tenth embodiment of the present invention will be described below.

Figure 35:
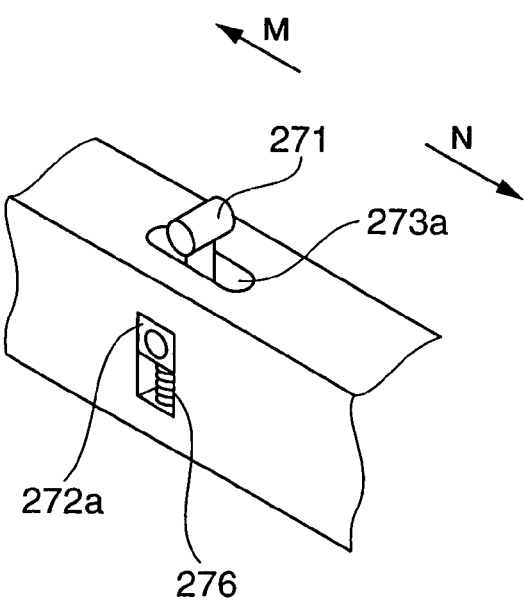
FIG. 35 is a main-part external enlarged perspective view illustrating the operation switch in the needle driver of a tenth embodiment of the present invention.
Figure 36:
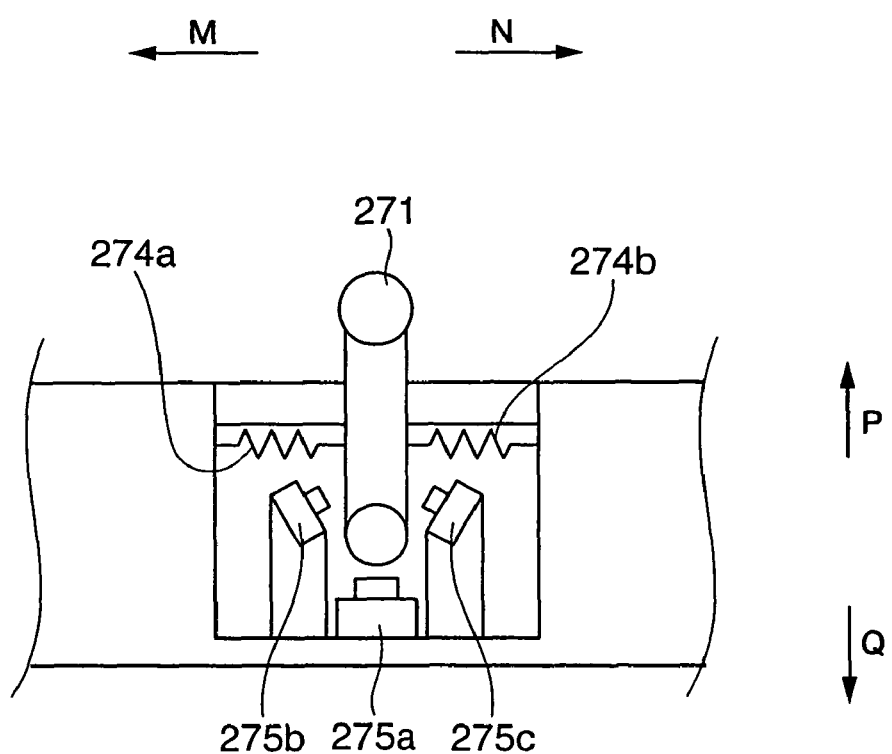
FIG. 36 is a main-part enlarged perspective view illustrating the opening and closing force generation switch and a turn force generation switch in the needle driver of the tenth embodiment.

FIG. 35 and FIG. 36 relate to the tenth embodiment of the present invention. FIG. 35 is a main-part external enlarged perspective view illustrating the operation switch in the needle driver of the tenth embodiment of the present invention. FIG. 36 is a main-part enlarged perspective view illustrating the opening and closing force generation switch and a turn force generation switch in the needle driver of the tenth embodiment.

Because the basic structure of the needle driver of the tenth embodiment is identical to that of the sixth embodiment, only the difference therebetween will be explained and the explanation of identical components will be omitted.

That is, the needle driver of the eighth embodiment differs from the needle driver of the sixth embodiment only in the portion of operation switches, wherein motors are the generation sources of the opening and closing force and turn force in the sixth embodiment. Other features are identical to those of the sixth embodiment. For example, the opening and closing force generation mechanism and turn force generation mechanism have a structure identical to those of the needle driver of the sixth embodiment, which is shown in FIG. 29.

As shown in FIG. 35 and FIG. 36, the needle driver of the tenth embodiment comprises an operation stick 271 serving as a switch for opening and closing force operation and switch for turn force operation in the operation unit 2.

The operation stick 271 has a shaft-like lower end, and both ends thereof are freely turnably supported by sliding bearings 272a, 272b. The sliding bearings 272a, 272b are provided so that the sliding bearings can slide in the up-down direction (shown by arrows P, Q in FIG. 36) inside long holes 273a, 273b drilled in the side surfaces of the operation unit 2 and impelled toward the upper side inside the long holes 273a, 273b by springs 276a, 276b attached to the outer sides of the lower ends of the sliding bearings 272a, 272b.

Springs 274a, b of which respective one side is fixed to the inner side of the operation unit 2 are provided at the distal end side and end back side of the operation stick 271 and, in a state where no force is applied, the springs are held so as to stand still in the direction perpendicular to the long axis direction of the operation unit 2.

Furthermore, a contact switch 275*a* is fixed to the lower end of the operation stick 271, and the contact switch 275*a* is connected to the control panel 213 (see FIG. 29). Moreover, contact switches 275*b*, 275*c* are fixed to the distal end side and end back side of the operation stick 271, and those contact switches 275*b*, 275*c* are also connected to the control panel 213.

In the needle driver of the tenth embodiment, when the operation stick 271 is pressed toward the lower end side (direction of arrow Q), the lower end of the operation stick 271 presses the contact switch 275*a*. Accordingly, the control panel 213 unidirectionally turns and drives the opening and closing motor 216 in the direction of opening the treatment unit 4. Furthermore, when the pressing action on the operation stick 271 is released in a state with the treatment unit 4 open, the control panel 213 turns and drives the opening and closing motor 216 in the other direction till the treatment unit 4 is closed.

On the other hand, when the operation stick 271 is tilted toward the distal end side (direction shown by arrow M in the figure), the operation stick 271 presses the contact switch 275*b*. Accordingly, the control panel 213 drives the turn motor 215 so that the treatment unit 4 turns in the same direction as the turn direction caused by the inclination of the operation stick 271.

Furthermore, when the operation stick 271 is tilted toward the end back side (direction shown by arrow N in the figure), the operation stick 271 presses the contact switch 275*c*. Accordingly, the control panel 213 drives the turn motor 215 so that the treatment unit 4 turns in the same direction as the other turn direction caused by the inclination of the operation stick 271.

With the needle driver of the tenth embodiment, when the opening closing operation and turn operation of the treatment unit are carried out, it is not necessary to remove a finger from the operation unit, the operations are easy to conduct, and the fatigue of the doctor is low. As a result, the patient can undergo high-quality surgery, the stay period of the patient in the hospital is shortened, the patient can be rapidly returned to society, the turnaround efficiency of beds for hospitalized patients is increased, and effective hospital management can thus be realized.

As described hereinabove, in accordance with the present invention, the surgery operation performed by a doctor is facilitated, the surgery time is reduced, and surgery quality is improved. As a result, the burden on the patient is reduced, the stay period of the patient in the hospital is shortened, the patient can be rapidly returned to society, and the effective hospital management can be realized.

The present invention is not limited to the above-described embodiments, and it goes without saying that various changes or applications are possible without departing form the essence of the present invention.

What is claimed is:

1. A surgical instrument comprising:
   an insertion unit;
   a treatment unit provided at one end of the insertion unit, capable of turning about a first turn axis which is perpendicular to a long axis of the insertion unit, and comprising a clamping section capable of an opening and closing action;
   an operation unit, which can be operated with a single finger and its long axis is the same as the long axis of the insertion unit, provided at the other end of the insertion unit;
   a turn force transmission mechanism, provided between the operation unit and the treatment unit along the insertion unit, and transmitting a turn force as a force to turn the treatment unit from the operation unit to the treatment unit;
   an opening and closing force transmission mechanism, provided between the operation unit and the treatment unit along the insertion unit, and transmitting an opening and closing force as a force to open and close the clamping section from the operation unit to the treatment unit; and
   a common operation mechanism, provided in the operation unit, which can generate the turn force transmitted by the turn force transmission mechanism and which can also generate the opening and closing force transmitted by the opening and closing transmission mechanism, wherein
   the common operation mechanism comprises a disk-shaped operation dial which is capable of turning about a second turn axis which is parallel to the first turn axis of the treatment unit;
   the turn force is generated by the turn operation of the operation dial, and the opening and closing force is generated by another operation different from the turn operation of the operation dial; and
   the other operation is an operation based on application of a pressing force to the operation dial in the direction perpendicular to the turn axis of the operation dial and on release of the application.

2. The surgical instrument according to claim 1, wherein the opening and closing force transmission mechanism has a displacement direction conversion mechanism that converts a displacement of the operation dial in a short axis direction, by an operation of pressing the operation dial in the short axis direction of the operation unit, into a displacement of the operation unit in a long axis direction.

3. A surgical instrument comprising:
   an insertion unit;
   a treatment unit provided at one end of the insertion unit, capable of turning about a first turn axis which is perpendicular to a long axis of the insertion unit, and comprising a clamping section capable of an opening and closing action;
   an operation unit, which can be operated with a single finger and its long axis is the same as the long axis of the insertion unit, provided at the other end of the insertion unit;
   a turn force transmission mechanism, provided between the operation unit and the treatment unit along the insertion unit, and transmitting a turn force as a force to turn the treatment unit from the operation unit to the treatment unit;
   an opening and closing force transmission mechanism, provided between the operation unit and the treatment unit along the insertion unit, and transmitting an opening and closing force as a force to open and close the clamping section from the operation unit to the treatment unit; and
   a common operation mechanism, provided in the operation unit, which can generate the turn force transmitted by the turn force transmission mechanism and which can also generate the opening and closing force transmitted by the opening and closing transmission mechanism, wherein the common operation mechanism comprises a disk-shaped operation dial which is capable of turning about a second turn axis which is parallel to the first turn axis of the treatment unit;

the turn force is generated by the turn operation of the operation dial, and the opening and closing force is generated by another operation different from the turn operation of the operation dial; and the other operation is an operation of pressing operation dial in a short axis direction of the operation unit.

4. The surgical instrument according to claim 3, wherein the opening and closing force transmission mechanism has a displacement direction conversion mechanism that converts a displacement of the operation dial in a short axis direction of the operation unit, by an operation of pressing the operation dial in the short axis direction of the operation unit, into a displacement of the operation unit in the long axis direction of the operation unit.

5. A surgical instrument comprising:

an insertion unit;

a treatment unit provided at one end of the insertion unit and capable of executing a plurality of actions;

an operation unit, which can be operated with single finger and its long axis is the same as a long axis of the insertion unit, provided at the other end of the insertion unit;

a first force transmission mechanism, provided between the operation unit and the treatment unit along the insertion unit, and transmitting a first force that causes the treatment unit to execute one prescribed action to the treatment unit from the operation unit;

a second force transmission mechanism, provided between the operation unit and the treatment unit along the insertion unit, and transmitting a second force that causes the treatment unit to execute another action that is different from the one action to the treatment unit from the operation unit; and a common operation mechanism, provided in the operation unit, which can generate the first force transmitted by the first force transmission mechanism and which can also generate the second force transmitted by the second force transmission mechanism, wherein the common operation mechanism comprises a disk-shaped operation dial which is capable of turning about a turn axis which is perpendicular to the long axis of the insertion unit;

the first force is generated by the turn operation of the operation dial, and the second force is generated by another operation different from the turn operation of the operation dial; and the other operation is based on application of a pressing force to the operation dial in the direction perpendicular to the turn axis of the operation dial and on release of the application.

6. The surgical instrument according to claim 5, wherein the second force transmission mechanism has a displacement direction conversion mechanism that converts a displacement of the operation dial in a short axis direction of the operation unit, by an operation of pressing the operation dial in the short axis direction of the operation unit, into a displacement of the operation unit in the long axis direction of the operation unit.

7. A surgical instrument comprising:

an insertion unit;

a treatment unit provided at one end of the insertion unit and capable of executing a plurality of actions;

an operation unit, which can be operated with single finger and its long axis is the same as a long axis of the insertion unit, provided at the other end of the insertion unit;

a first force transmission mechanism, provided between the operation unit and the treatment unit along the insertion unit, and transmitting a first force that causes the treatment unit to execute one prescribed action to the treatment unit from the operation unit;

a second force transmission mechanism, provided between the operation unit and the treatment unit along the insertion unit, and transmitting a second force that causes the treatment unit to execute another action that is different from the one action to the treatment unit from the operation unit; and a common operation mechanism, provided in the operation unit, which can generate the first force transmitted by the first force transmission mechanism and which can also generate the second force transmitted by the second force transmission mechanism, wherein the common operation mechanism comprises a disk-shaped operation dial which is capable of turning about a turn axis which is perpendicular to the long axis of the insertion unit;

the first force is generated by the turn operation of the operation dial, and the second force is generated by another operation different from the turn operation of the operation dial; and the other operation is an operation of pressing the operation dial in a short axis direction of the operation unit.

8. The surgical instrument according to claim 7, wherein the second force transmission mechanism has a displacement direction conversion mechanism that converts a displacement of the operation dial in a short axis direction, by an operation of pressing the operation dial in the short axis direction of the operation unit, into a displacement of the operation unit in a long axis direction.

9. A surgical instrument comprising:

an insertion unit;

a treatment unit provided at one end of the insertion unit, capable of turning about a first turn axis which is perpendicular to a long direction of the insertion unit, and comprising a clamping section capable of opening and closing action;

an operation unit, which can be operated with a single finger and its long axis is the same as the long axis of the insertion unit, provided at the other end of the insertion unit;

turn force transmission means, provided between the operation unit and the treatment unit along the insertion unit, and transmitting a turn force as a force to turn the treatment unit from the operation unit to the treatment unit;

opening and closing force transmission means, provided between the operation unit and the treatment unit along the insertion unit, and transmitting an opening and closing force as a force to open and close the clamping section from the operation unit to the treatment unit; and common operation means, provided in the operation unit, which can generate the turn force transmitted by the turn force transmission means and which can also generate the opening and closing force transmitted by the opening and closing transmission means, wherein the common operation means comprises a disk-shaped operation dial which is capable of turning about a second turn axis which is parallel to the first turn axis of the treatment unit;

the turn force is generated by the turn operation of the operation dial, and the opening and closing force is generated by another operation different from the turn operation of the operation dial; and the other operation is based on application of a pressing force to the operation dial in the direction perpendicular to the turn axis of the operation dial and on release of the application.

10. The surgical instrument according to claim 9, wherein the opening and closing force transmission means has displacement direction conversion means that converts a displacement of the operation dial in a short axis direction of the operation unit, by an operation of pressing the operation dial in the short axis direction of the operation unit, into a displacement of the operation unit in the long axis direction of the operation unit.

11. A surgical instrument comprising:

an insertion unit;

a treatment unit provided at one end of the insertion unit, capable of turning about a first turn axis which is perpendicular to a long direction of the insertion unit, and comprising a clamping section capable of opening and closing action;

an operation unit, which can be operated with a single finger and its long axis is the same as the long axis of the insertion unit, provided at the other end of the insertion unit;

turn force transmission means, provided between the operation unit and the treatment unit along the insertion unit, and transmitting a turn force as a force to turn the treatment unit from the operation unit to the treatment unit;

opening and closing force transmission means, provided between the operation unit and the treatment unit along the insertion unit, and transmitting an opening and closing force as a force to open and close the clamping section from the operation unit to the treatment unit; and common operation means, provided in the operation unit, which can generate the turn force transmitted by the turn force transmission means and which can also generate the opening and closing force transmitted by the opening and closing transmission means, wherein the common operation means comprises a disk-shaped operation dial which is capable of turning about a second turn axis which is parallel to the first turn axis of the treatment unit;

the turn force is generated by the turn operation of the operation dial, and the opening and closing force is generated by another operation different from the turn operation of the operation dial; and the other operation is an operation of pressing operation dial in a short axis direction of the operation unit.

12. The surgical instrument according to claim 11, wherein the opening and closing force transmission means has displacement direction conversion means that converts a displacement of the operation dial in the short axis direction of the operation unit, by an operation of pressing the operation dial in the short axis direction of the operation unit, into a displacement of the operation unit in the long axis direction of the operation unit.

13. A surgical instrument comprising:

an insertion unit;

a treatment unit provided at one end of the insertion unit and capable of executing a plurality of actions;

an operation unit, which can be operated with a single finger and its long axis is the same as a long axis of the insertion unit, provided at the other end of the insertion unit;

first force transmission means, provided between the operation unit and the treatment unit along the insertion unit, and transmitting a first force that causes the treatment unit to execute one prescribed action to the treatment unit from the operation unit;

second force transmission means, provided between the operation unit and the treatment unit along the insertion unit, and transmitting a second force that causes the treatment unit to execute another action that is different from the one action to the treatment unit from the operation unit; and common operation means, provided in the operation unit, which can generate the first force transmitted by the first force transmission means and which can also generate the second force transmitted by the second force transmission means, wherein the common operation means comprises a disk-shaped operation dial which is capable of turning about a turn axis;

the first force is generated by the turn operation of the operation dial, and the second force is generated by another operation different from the turn operation of the operation dial; and the other operation is based on application of a pressing force to the operation dial in the direction perpendicular to the turn axis of the operation dial and on release of the application.

14. The surgical instrument according to claim 13, wherein the second force transmission means has displacement direction conversion means that converts a displacement of the operation dial in a short axis direction of the operation unit, by an operation of pressing the operation dial in the short axis direction of the operation unit, into a displacement of the operation unit in the long axis direction of the operation unit.

15. A surgical instrument comprising:

an insertion unit;

a treatment unit provided at one end of the insertion unit and capable of executing a plurality of actions;

an operation unit, which can be operated with a single finger and its long axis is the same as a long axis of the insertion unit, provided at the other end of the insertion unit;

first force transmission means, provided between the operation unit and the treatment unit along the insertion unit, and transmitting a first force that causes the treatment unit to execute one prescribed action to the treatment unit from the operation unit;

second force transmission means, provided between the operation unit and the treatment unit along the insertion unit, and transmitting a second force that causes the treatment unit to execute another action that is different from the one action to the treatment unit from the operation unit; and common operation means, provided in the operation unit, which can generate the first force transmitted by the first force transmission means and which can also generate the second force transmitted by the second force transmission means, wherein the common operation means comprises a disk-shaped operation dial which is capable of turning about a turn axis;

the first force is generated by the turn operation of the operation dial, and the second force is generated by another operation different from the turn operation of the operation dial; and the other operation is an operation of pressing the operation dial in a short axis direction of the operation unit.

16. The surgical instrument according to claim 15, wherein the second force transmission means has displacement direction conversion means that converts a displacement of the operation dial in a short axis direction of the operation unit, by an operation of pressing the operation dial in the short axis direction of the operation unit, into a displacement of the operation unit in the long axis direction of the operation unit.

\* \* \* \* \*